US012014820B2

(12) United States Patent
Talmor et al.

(10) Patent No.: US 12,014,820 B2
(45) Date of Patent: *Jun. 18, 2024

(54) SUBTLE WEARABLE HEALTH SUPPORT SYSTEMS AND METHODS

(71) Applicant: Amoa Group Inc., Miami, FL (US)

(72) Inventors: Avihay Talmor, Los Angeles, CA (US); Avraham Ariel Zadok, Los Angeles, CA (US); Oriana Virginia Torres Fuenmayor, Miami, FL (US); Beata Kouchnir, Seaattle, WA (US); Harshil Haumeer, Seattle, WA (US); Jonathan E. Olson, Bellevue, WA (US)

(73) Assignee: Amoa Group Inc.

( * ) Notice: Subject to any disclaimer, the term of this patent is extended or adjusted under 35 U.S.C. 154(b) by 115 days.

This patent is subject to a terminal disclaimer.

(21) Appl. No.: 17/688,413

(22) Filed: Mar. 7, 2022

(65) Prior Publication Data

US 2022/0415499 A1     Dec. 29, 2022

Related U.S. Application Data

(63) Continuation-in-part of application No. 17/362,680, filed on Jun. 29, 2021, now Pat. No. 11,270,796.

(51) Int. Cl.
*G16H 40/67* (2018.01)

(52) U.S. Cl.
CPC .................. *G16H 40/67* (2018.01)

(58) Field of Classification Search
CPC ........ G16H 40/67; G16H 20/60; G16H 20/70; G16H 40/63; G16H 50/20; G16H 50/70; G16H 10/20; G08B 21/245
See application file for complete search history.

(56) References Cited

U.S. PATENT DOCUMENTS

| 10,736,566 | B2* | 8/2020 | Sazonov | A61B 7/001 |
|---|---|---|---|---|
| 10,790,054 | B1* | 9/2020 | Vleugels | A61B 5/1114 |
| 11,270,796 | B1* | 3/2022 | Talmor | G16H 40/63 |
| 2017/0249445 | A1* | 8/2017 | Devries | A61B 5/145 |

* cited by examiner

*Primary Examiner* — Toan N Pham
(74) *Attorney, Agent, or Firm* — AEON Law, PLLC; Adam L. K. Philipp; Jonathan E. Olson

(57) ABSTRACT

Haptic reminders and related technologies are described in which a wearable first article receives a rule. In some variants the rule was used in a second article and the delivery is programmatically conditioned upon one or more articles like the second article having worked well enough with the rule. The received rule occasionally triggers haptic energy via the first article to remind the wearer to eat more slowly, hydrate or exercise more often, or otherwise perform better. Such reminders may serve other purposes or be conditionally extended if a wearer does not improve. Other improved modes of discernment and notification are also presented.

17 Claims, 13 Drawing Sheets

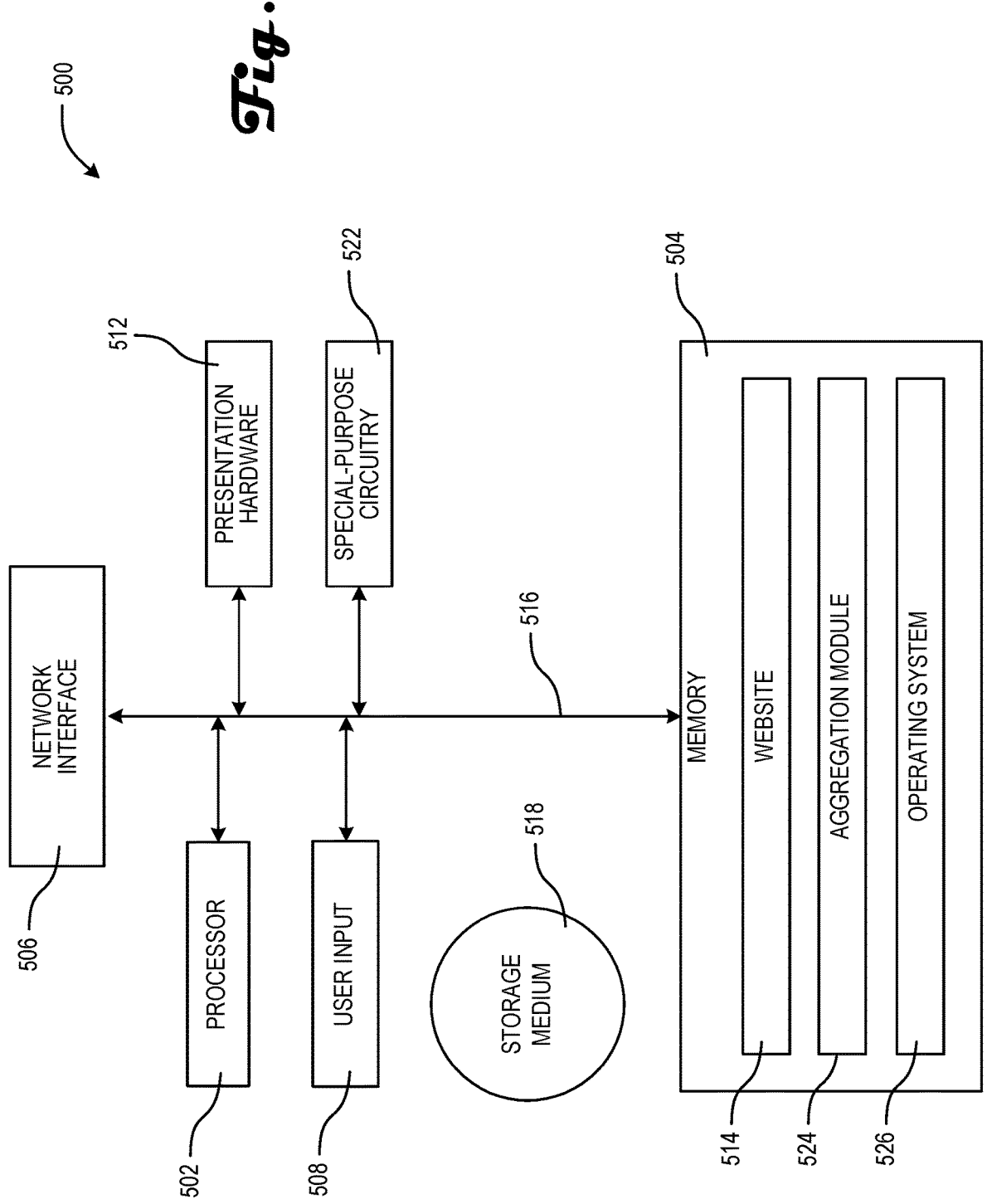

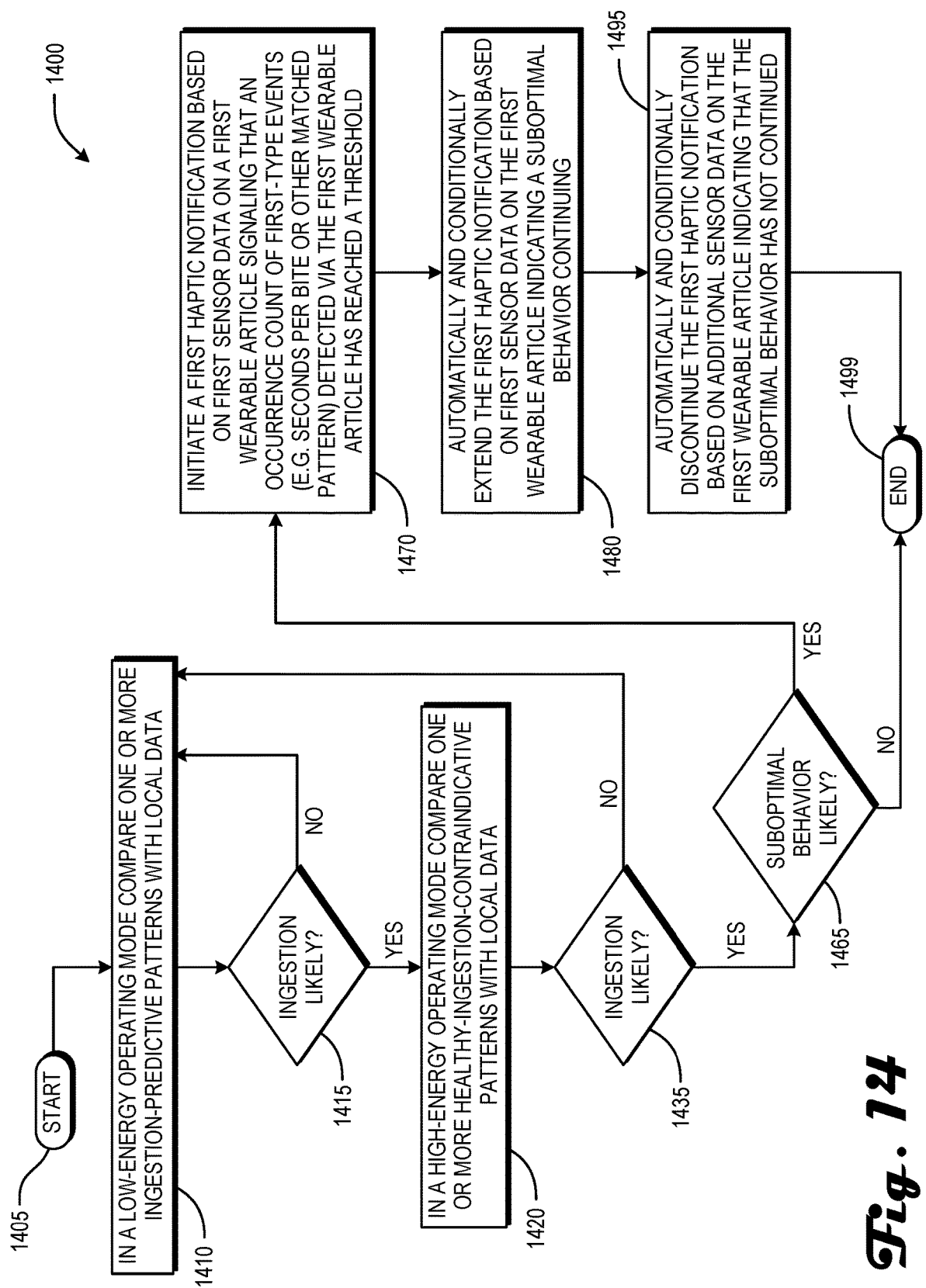

SUBTLE WEARABLE HEALTH SUPPORT SYSTEMS AND METHODS

RELATED APPLICATIONS

The present application is related to U.S. application Ser. No. 17/362,680, now U.S. Pat. No. 11,270,796, filed on 29 Jun. 2021 entitled "SUBTLE WEARABLE HEALTH SUPPORT SYSTEMS AND METHODS."

BRIEF DESCRIPTION OF THE DRAWINGS

FIG. 5 depicts a server in which one or more improved technologies may be incorporated.

FIG. 14 depicts an operational flow for use in a wearable article according to one or more improved technologies.

DETAILED DESCRIPTION

Figure 1:
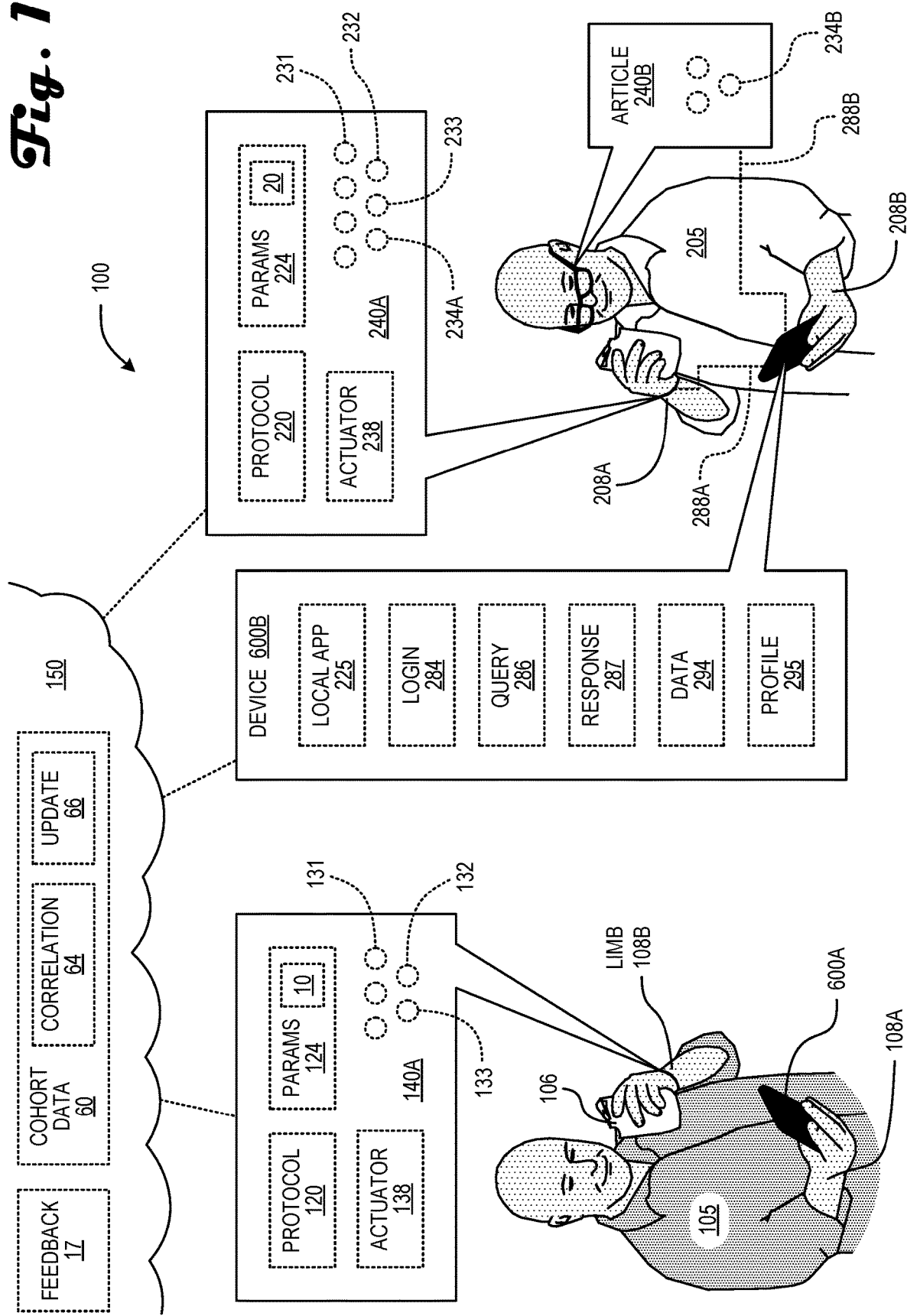
FIG. 1 depicts wearers of first-type and second-type articles according to one or more improved technologies.

The detailed description that follows is represented largely in terms of processes and symbolic representations of operations by conventional computer components, including a processor, memory storage devices for the processor, connected display devices, and input devices. Furthermore, some of these processes and operations may utilize conventional computer components in a heterogeneous distributed computing environment, including remote file servers, computer servers, and memory storage devices.

It is intended that the terminology used in the description presented below be interpreted in its broadest reasonable manner, even though it is being used in conjunction with a detailed description of certain example embodiments. Although certain terms may be emphasized below, any terminology intended to be interpreted in any restricted manner will be overtly and specifically defined as such.

The phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise. "Aboard," "actual," "a set of," "aboard," "above," "additional," "adjusted," "adopted," "after," "against," "allowed," "also," "alternatively," "any," "article-specific," "artificial intelligence," "associated," "at least," "automatic," "auxiliary," "average," "better," "Boolean," "bounded," "but so," "calibrated," "captured," "caused," "central," "characterized," "chewing," "collectively," "conditional," "configured," "context-specific," "continued," "corresponding with," "counterpart," "crossing," "crowd-sourced," "deemed," "depicting," "deployed," "described," "detected," "directly," "distilled," "distributed," "duplicated," "each," "eating," "energy-saving," "established," "evaluator-assigned," "explicit," "faster," "first," "from," "haptic," "having," "human," "ideal," "identical," "idiothetic," "implemented by," "in," "including," "incremental," "indicated," "initiating," "jointly," "kinematic," "larger," "learning," "local," "manual," "matched," "mechanically," "more than," "nominal," "normal," "numerous," "obtained via," "of," "operably coupled," "optimal," "otherwise," "particular," "partly," "passed," "pertaining to," "photographic," "preparatory," "previous," "primary," "prior," "programmatic," "reached," "received," "recorded," "regional," "relating to," "remote," "reordered," "residing in," "rule-based," "said," "satisfactory," "satisfied," "scalar," "scoring," "second," "second," "secondary," "serving," "signaling," "similar," "simultaneous," "slurping," "so as to," "suboptimal," "success-indicative," "supported," "tertiary," "the same," "thereafter," "third," "threshold," "too low," "triggered," "updated," "used," "variant," "via," "wearable," "well," "wherein," "within," "without any regard to," "working," "worthy," or other such descriptors herein are used in their normal yes-or-no sense, not merely as terms of degree, unless context dictates otherwise. In light of the present disclosure, those skilled in the art will understand from context what is meant by "remote" and by other such positional descriptors used herein. Likewise they will understand what is meant by "partly based" or other such descriptions of dependent computational variables/signals. "Numerous" as used herein refers to more than two dozen. "Instantaneous" as used herein refers to having a duration of less than 0.1 seconds unless context dictates otherwise. "Immediate" as used herein refers to having a duration of less than 2 seconds unless context dictates otherwise. Circuitry or data items are "onboard" as used herein if they are aboard a wearable or other mobile device unless context dictates otherwise. Circuitry is "invoked" as used herein if it is called on to undergo voltage state transitions so that digital signals are transmitted therefrom or therethrough unless context dictates otherwise. Software is "invoked" as used herein if it is executed/triggered unless context dictates otherwise. One number is "on the order" of another if they differ by less than an order of magnitude (i.e., by less than a factor of ten) unless context dictates otherwise. As used herein "causing" is not limited to a proximate cause but also enabling, conjoining, or other actual causes of an event or phenomenon.

Terms like "processor," "center," "unit," "computer," or other such descriptors herein are used in their normal sense, in reference to an inanimate structure. Such terms do not include any people, irrespective of their location or employment or other association with the thing described, unless context dictates otherwise. "For" is not used to articulate a mere intended purpose in phrases like "circuitry for" or "instruction for," moreover, but is used normally, in descriptively identifying special purpose software or structures.

As used herein an "instance" of a thing may include a perfect copy. A copied "instance" of a digital object, for example, may become a new version by being modified or created so as to differ in composition from the prior second version. Not every new instance qualifies as a new "version," but every first and second versions of a digital object differ in composition. As used herein a "version" of a digital object refers to a variant having partial structural identicality with the object or partial functional identicality with the object (or both). As used herein a modification of a digital item may be "facilitated" by triggering, enabling, defining, signaling, or otherwise causing the modification (or a combination of these). As used herein a first value is "based on" a second value if the second value is a factor or other determinant of the first.

Reference is now made in detail to the description of the embodiments as illustrated in the drawings. While embodiments are described in connection with the drawings and related descriptions, there is no intent to limit the scope to the embodiments disclosed herein. On the contrary, the intent is to cover all alternatives, modifications and equivalents. In alternate embodiments, additional devices, or combinations of illustrated devices, may be added to, or combined, without limiting the scope to the embodiments disclosed herein.

FIG. 1 depicts a network 150 configured to coordinate activity among two or more human subjects 105, 205 who each (at respective moments) have an active limb 108B, 208A holding food 106 being eaten and a stationary limb 108A, 208B holding a mobile device 600A, 600B. The active limbs also support respective wearable articles 140A, 240A (e.g. smartwatches, bracelets, or mountable modules) that may have one or more matched protocols 120, 220; matched microphones 131, 231; matched accelerometers or other idiothetic kinematic sensors 132, 232; matched haptic actuators 138, 238; or other matched features as shown. Whether or not additional matched sensors 133, 233 as shown are provided or used, one or more components (e.g. a camera or other auxiliary sensor 234A) that were aboard a prototype or other complete article 240A are depopulated/absent from a streamlined counterpart article 140A (e.g. to increase battery life). Alternatively or additionally, one or more training data capture articles 240B operated in conjunction with article 240A may supply (synchronized and correlative data via) one or more extra sensors 234B thereof that are "auxiliary." As used herein a "auxiliary" sensor is one that is suitable to provide a context associated with captured training data that characterizes events or other aspects of a wearable article but that may lack a counterpart in a more basic or streamlined version of the article. As used herein "primary" sensor data includes data used within a wearable article or other "type" of apparatus that includes or otherwise houses one or more sensors (1) by which the "primary" sensor data was obtained and (2) that are each (nominally) identical to a counterpart sensor in another article or apparatus. As used herein "secondary" sensor data includes data that does not qualify as "primary" and that is from a counterpart sensor configured to be supported by a limb of a person. As used herein "auxiliary" sensor data includes data from an unmatched sensor or otherwise not qualifying as "primary" or "secondary."

One or more extra wireless linkages 288A-B as shown can likewise facilitate the aggregation of auxiliary data 294, such as in a mobile device 600B by which the subject 205 registers or downloads a local app 225 with a secure login 284. In some contexts such raw auxiliary data 294 allows one or more remote evaluators to glean timestamped attributes of a consumption context such as (1) whether a subject was actually ingesting; (2) what was being ingested; (3) in what environment it was being ingested; (4) whether it was being ingested with a fork, by hand, or by some other consumption mode; (5) whether it was being ingested too fast, too slow, or otherwise in some unhealthy manner; (6) whether the subject was pleased by or responsive to a particular reminder about such (an apparently) suboptimal consumption; or combinations of items like these. Such evaluators need not all be experts, but simply willing to and capable of using auxiliary data to provide reliable context for sensor data 20 as machine learning annotations. Such information can be aggregated over time in a profile 295, and for study participants or certain other volunteers, learning data can be made especially valuable with one or more queries 286 each matched to a reply 287 in a structured dialog. Alternatively or additionally, other feedback 17 about operational parameters 224 used aboard the second article 240A and resulting data 20 can likewise be distilled and compared with other cohort data 60 reflecting other instances of ingestion, other circumstances, and other observed behaviors so as to glean one or more correlations 64 as indicated below. Even if machine learning and enhanced protocols 220 thus available as updates 66 may take time by virtue of particular wearable articles 140A mostly remaining offline, operating parameters 124 and sensor data 10 for other such devices are expected to improve rapidly as field data continues to populate learning modules as described below. It is hoped and expected that this will reduce large numbers of false-positive errors (e.g. haptic misfires) or false-negative errors (e.g. missed opportunities for a desirable and appropriate haptic notification), for example, for protocols that use one or more haptic reminders for human behavior that is to be avoided or otherwise acknowledged in a programmatic manner.

Figure 2:
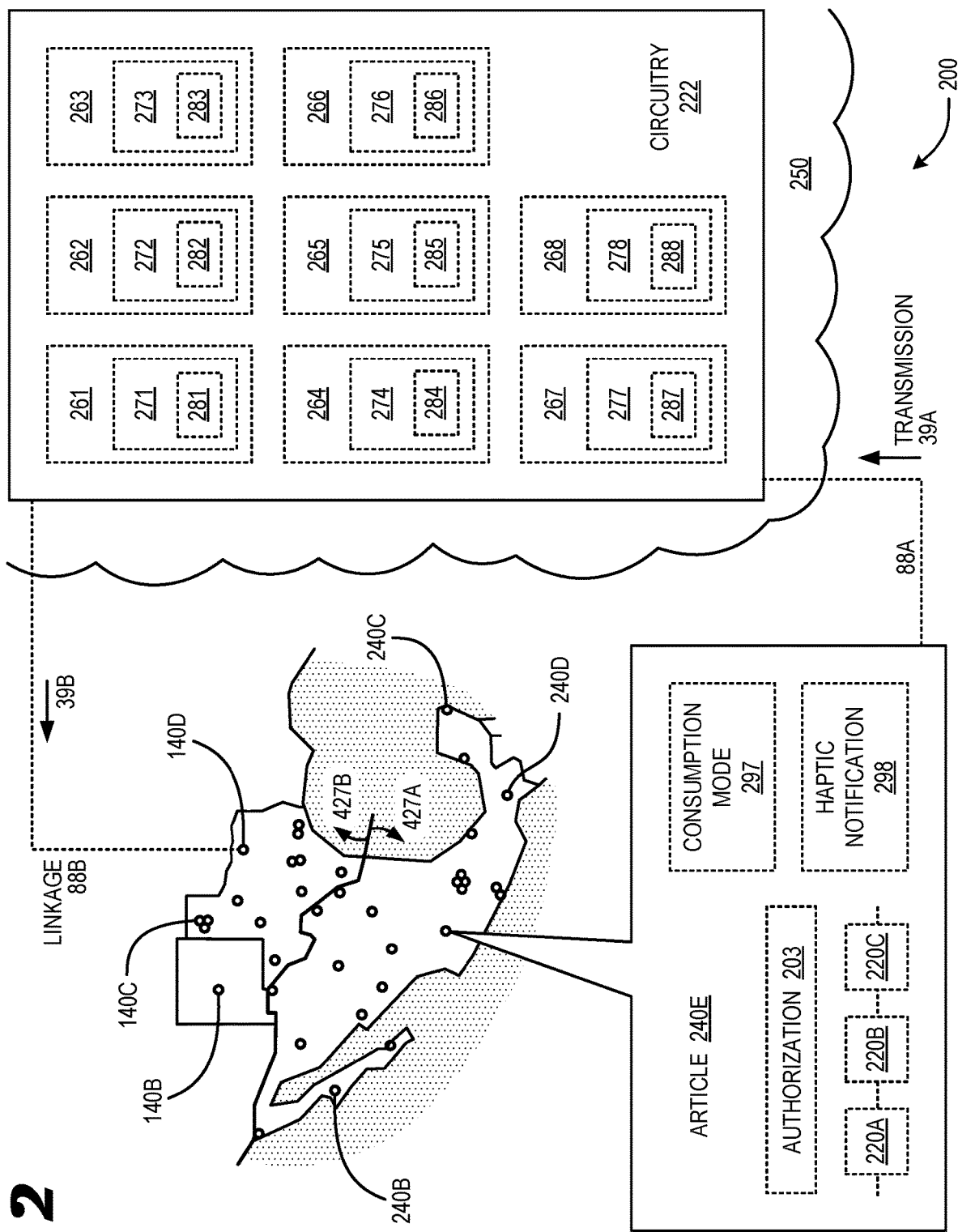
FIG. 2 depicts wearable articles in respective cohorts in which one or more improved technologies may be incorporated.

FIG. 2 schematically illustrates salient aspects of one or more distributed or other data-handling systems 200 configured to facilitate international monitoring and comprising transistor-based circuitry 222 in one or more data networks 250, in which one or more technologies may be implemented. In the interest of concision and according to standard usage in information management technologies, the functional attributes of modules described herein are set forth in natural language expressions. It will be understood by those skilled in the art that such expressions (functions or acts recited in English, e.g.) adequately describe structures identified below so that no undue experimentation will be required for their implementation. For example, any session parameters or other informational data identified herein may easily be represented digitally as a voltage configuration on one or more electrical nodes (conductive pads of an integrated circuit, e.g.) of an event-sequencing structure without any undue experimentation. Each electrical node is highly conductive, having a corresponding nominal voltage level that is spatially uniform generally throughout the node (within a device or local system as described herein, e.g.) at relevant times (at clock transitions, e.g.). Such nodes (lines on an integrated circuit or circuit board, e.g.) may each comprise a forked or other signal path adjacent one or more transistors. Moreover, many Boolean values (yes-or-no decisions, e.g.) may each be manifested as either a "low" or "high" voltage, for example, according to a complementary metal-oxide-semiconductor (CMOS), emitter-coupled logic (ECL), or other common semiconductor configuration protocol. In some contexts, for example, one skilled in the art will recognize an "electrical node set" as used herein in reference to one or more electrically conductive nodes upon which a voltage configuration (of one voltage at each node, for example, with each voltage characterized as either high or low) manifests a yes/no decision or other digital data.

Such circuitry 222 may comprise one or more integrated circuits (ICs), for example, optionally mounted on one or more circuit boards. Whether implemented in a distributed cloud or within one or more servers or other devices described herein, transistor-based circuitry 222 comprises an event-sequencing structure generally as described in U.S. Pat. Pub. No. 2015/0094046 but configured as described herein. Transistor-based circuitry 222 may (optionally) include one or more instances of invocation modules 261 configured to invoke one or more other modules 262-268 configured to perform a function, for example, each including a corresponding electrical node set 271 upon which informational data is represented digitally as a corresponding voltage configuration 281. (It should be noted that when a user or other signal originator "invokes" one or more modules 262-268 configured to perform a function, other circuitry along the signal path will also typically "invoke" circuitry downstream configured to perform that function, in a cascading fashion.) Transistor-based circuitry 222 may likewise include one or more instances of configuration modules 262 that prepare for or initiate remote or other processing, each including an electrical node set 272 upon which informational data is represented digitally as a corresponding voltage configuration 282. Transistor-based circuitry 222 may (optionally) likewise include one or more instances of distillation modules 263 configured for triggering local or other processing, each including an electrical node set 273 upon which informational data is represented digitally as a corresponding voltage configuration 283. Transistor-based circuitry 222 may likewise include one or more instances of authorization modules 264 configured for triggering local or other processing, each including an electrical node set 274 upon which informational data is represented digitally as a corresponding voltage configuration 284. Transistor-based circuitry 222 may likewise include one or more instances of control modules 265 configured for triggering local or other processing, each including an electrical node set 275 upon which informational data is represented digitally as a corresponding voltage configuration 285. Transistor-based circuitry 222 may likewise include one or more instances of recognition modules 266 configured for recognizing events or other patterns, each including an electrical node set 276 upon which informational data is represented digitally as a corresponding voltage configuration 286. Transistor-based circuitry 222 may likewise include one or more instances of (neural networks or other machine) learning modules 267 configured for configuring local or other event-sequencing logic, each including an electrical node set 277 upon which informational data is represented digitally as a corresponding voltage configuration 287. Transistor-based circuitry 222 may likewise include one or more instances of deployment modules 268 configured for configuring local or other event-sequencing logic, each including an electrical node set 278 upon which informational data is represented digitally as a corresponding voltage configuration 288. However such circuitry 222 is installed or arranged it will be understood that reconfiguring the arrangement for convenient performance or geography is contemplated as described herein according to the scope and spirit of respective inventions described.

Several scenarios are described herein in which one context 427A for events (e.g. Mexico or Latin America) is meaningfully distinct from another context 427B (e.g. Texas or the continental United States). Cuisines, dialects, customs, and other cultural norms may differ markedly across such geographic divides, as well as between populous and rural zones. Data 10 pertaining to first-type articles 140A-D (often excluding context-indicative data 294) may not be as rich as data 20 pertaining to second-type articles 240A-E (often including context-indicative data 294). To address various aspects of these differences, article 240E is depicted with an authorization 203 (e.g. from a wearer that chose to allow article 240E to share sensor, context, and event data 20) to flow as a wireless transmission 39A across linkage 88A. This may occur, for example, in a context in which a consumption mode 297 (e.g. whether a straw is used or food 106 is held with a utensil or an underhand grip) is digitally recorded along with whether, when, and how a haptic notification 298 is delivered via the article 240E; in which particular distillations as described herein are included in transmission 39A; and in which one or more human or other decision-making entities are thereby able to respond with an update or similar transmission 39B (e.g. via linkage 88B) to one or more first-type articles 140 and also to one or more second-type articles 240 (e.g. as a broadcast update to articles in use by registered study participants).

Figure 3:
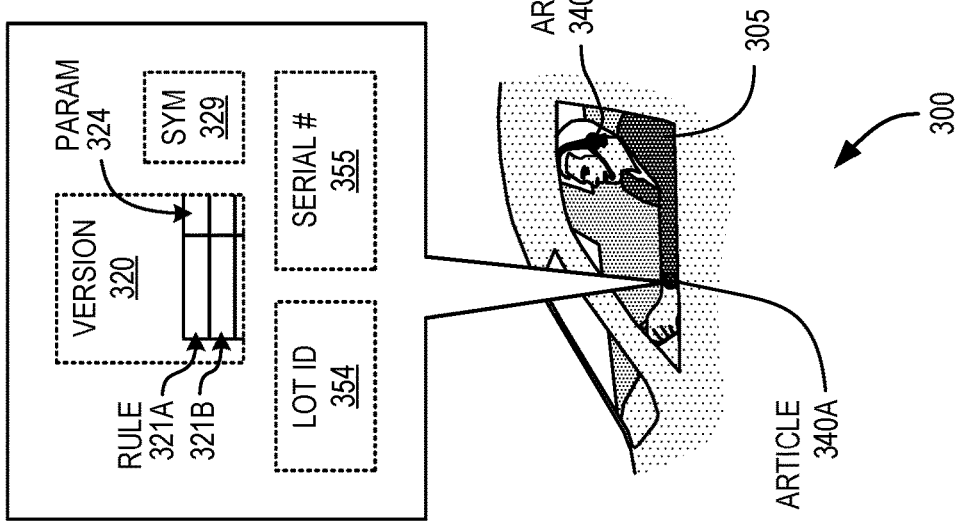
FIG. 3 depicts a human subject wearing articles in which one or more improved technologies may be incorporated.

FIG. 3 depicts a human subject 305 wearing one or more articles 340A-B configured to detect events as described below and to respond with haptic notifications 298 of various conditions each with corresponding explanatory content. Such haptic notifications 298 may comprise haptically distinguishable symbols 329 (e.g. each made of 2-10 human-perceivable pulses) respectively signaling to a human subject 105, 305, 805A who is wearing the first wearable article (1) that the wearer is eating too fast or otherwise expressing a suboptimal behavior, (2) that the wearer has completed a meal or other task without any suboptimal behavior, or (3) providing a special-case remedial notification to the wearer. This can occur, for example, in a context in which a first haptic notification 298 comprises one or more repetitions of a first Morse Code character or other informational pulse sequence that distinctly signals (that the wearer was apparently engaged in) a suboptimal behavior; in which at least one other haptic notification 298 comprises a second Morse Code character that distinctly signals (that the wearer has apparently completed) a meal or other task without any suboptimal behavior, in which on another day a haptic notification 298 comprises a third Morse Code character as a reminder that the first wearable article 140, 340A should be worn on a limb 108B that is not used for steering a motor vehicle and is used instead for eating or drinking; and in which the respective symbols 329 are haptically distinguishable from one another. In a "new user" protocol such notifications may be accompanied by brief audible or visual explanatory components, for example, if provided as a 1-2 second message presented via a display screen of a wrist-worn article 340A or a speaker of another wearable article 340B or handheld device 600.

It also deserves emphasis that in some variants article 340A is likewise digitally recognizable as having an alphanumeric lot identifier 354 by which one or more records can track hardware or other attributes of a set of first-, second-, or third-type articles as further described below. Moreover such articles may likewise include a digitally recognizable alphanumeric serial number 355 or other unique identifier by which one or more records can track a current protocol version 320 or other attributes of a wearable article individually as through one or more updates as further described below. See FIG. 8.

Figure 4:
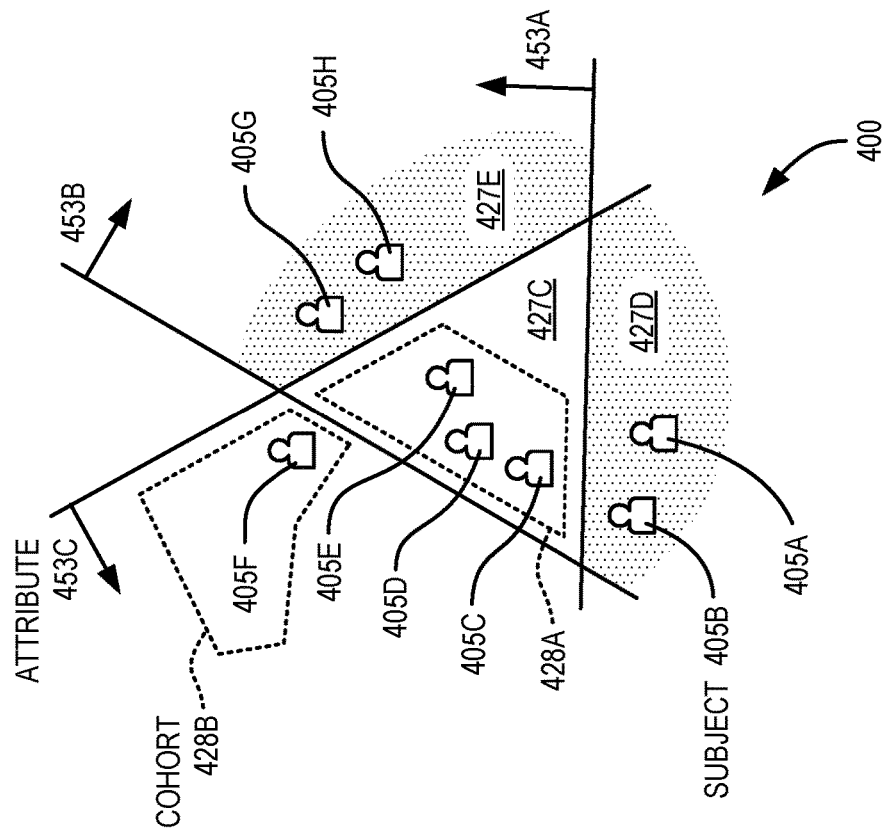
FIG. 4 depicts demographic, behavioral, and other contextual attributes as a Venn Diagram in which one or more improved partitioning technologies may be incorporated.

FIG. 4 depicts behavioral and other attributes of respective human cohorts 428A-B in a contextual Venn Diagram in which one or more improved technologies may be incorporated. As shown some defined consumption modes 297 may specify an attribute 453A (e.g. gleaned or posited from camera, microphone, or other supporting data 294) relating to a noisy distracting environment being present during a recorded event or other behavior of one or more subjects 405A-H each in a particular context 427C-E. Subjects 405A-B as shown, for example, are treated as not being in a behavioral context 427D influenced by any such apparent distraction (e.g. eating in a quiet place). Likewise as shown some consumption modes 297 may specify an attribute 453B (e.g. gleaned or posited from Global Positioning System coordinates, accelerometer data, or other supporting data 294) relating to an apparent personal travel motion being present during a recorded event or other behavior. And subject 405F as shown is treated as not being in a behavioral context 427D influenced by any such apparent motion (e.g. eating while apparently not traveling). Likewise as shown some consumption modes 297 may specify an attribute 453 (e.g. gleaned or posited from auxiliary tiltometer or other supporting data 294) relating to an apparent sandwich-grip being present during a recorded eating event or other particular behavior of interest. And subjects 405G-H as shown are treated as not using any such grip while their active limbs signal activity (e.g. eating with a hand held at an angle that suggests a utensil or cup was used for consumption). By defining such contexts 427A-E with such high granularity (e.g. of one or more such attributes 427 used to describe a behavioral context 427 so as to exclude one or more other kinds of context 427), noise present even in streamlined "first" wearable articles 140 will become less and less of an obstacle to accurate inferences as larger context-specific data sets become available across articles 140, 240, 340 with matched sensors or haptic actuators (or both). This can occur, for example, in a context in which large variances resulting from contextually heterogeneous and dirty sensor data 702 are supplanted by smaller variances resulting from dirty sensor data 702 that is contextually more homogeneous; in which a most permissive range 745 of "optimal" rates 765 is selected so as to create a just-large-enough composite range 745; and in which an inappropriately large composite range 745 would otherwise (create a "false negative" so as to) waste an opportunity to provide a haptic notification 298 that is truly indicative of a suboptimal rate 765. Moreover a fractional scalar distillation 778 (such as a tercile, median, or other percentile) may be advantageous for preventing sensor data 702 from an eating contest, for example, from tainting a heuristically derived threshold 752 that bounds "optimal" from "too fast" in some contexts.

More generally some operating parameters 224, 324 (e.g. thresholds) or other aspects of protocols 120, 220 described herein may be provided by one or more intelligence-amplified or specialist human users (not shown) who have received one or more context-enriched data distillations (e.g. empirical correlations 64) that have been partitioned by one or more demographic, geographic, behavioral, kinematic, or other cohort/event attributes 453 that selectively include some of said one or more distillations and excludes others. See FIGS. 7-13. Alternatively or additionally such hypotheses, tests, outcomes, or results may be used by machine learning modules 267 or other such entities to maximize an effectiveness of such distillations as described herein without much experimentation.

Referring now to FIG. 5, there is shown a server 500 in which one or more technologies may be implemented. Server 500 may include one or more instances of processors 502, of memories 504, user inputs 508, and of (speakers or other) presentation hardware 512 all interconnected along with the network interface 506 via a bus 516. One or more network interfaces 506 allow server 500 to connect via the Internet or other networks 150). Memory 504 generally comprises a random-access memory ("RAM"), a read only memory ("ROM"), and a permanent mass storage device, such as a disk drive.

Memory 504 may contain one or more instances of web sites 514, of aggregation modules 524, or of operating systems 526. These and other software components may be loaded from a non-transitory computer readable storage medium 518 into memory 504 of the server 500 using a drive mechanism (not shown) associated with a non-transitory computer readable storage medium 518, such as a floppy disc, tape, DVD/CD-ROM drive, flash card, memory card, or the like. In some embodiments, software or other digital components may be loaded via the network interface 506, rather than via a computer readable storage medium 518. Special-purpose circuitry 522 may, in some variants, include some or all of the event-sequencing logic described herein. In some embodiments server 500 may include many more components than those shown in FIG. 5, but it is not necessary that all conventional components of a server be shown in order to disclose an illustrative embodiment.

Figure 6:
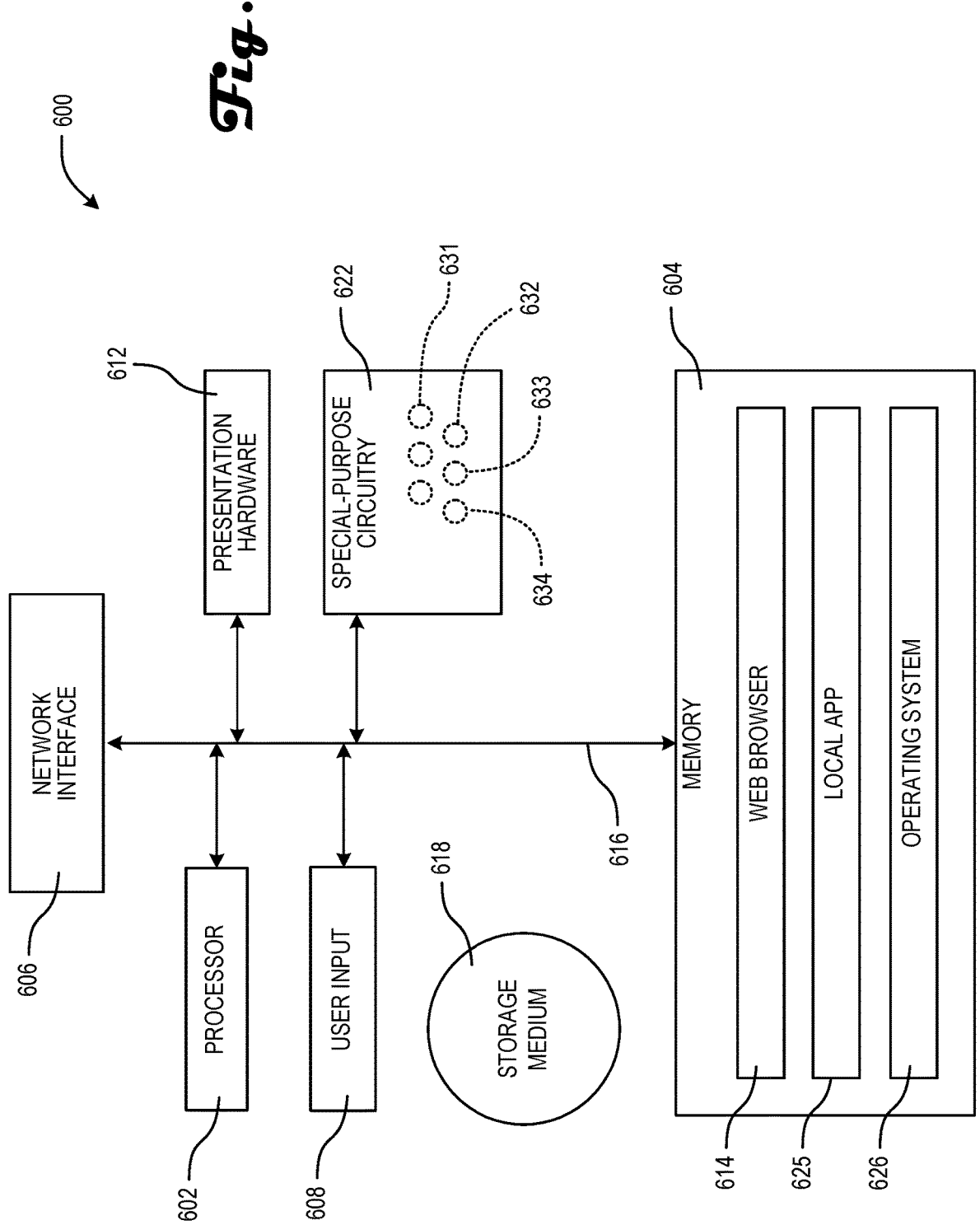
FIG. 6 depicts a wearable or other client device in which one or more improved technologies may be incorporated.

Referring now to FIG. 6, there is shown a client device 600 in which one or more technologies may be implemented. Device 600 may include one or more instances of processors 602, of memories 604, user inputs 608, and of (speakers or other) presentation hardware 612 all interconnected along with the network interface 606 via a bus 616. One or more network interfaces 606 allow device 600 to connect via the Internet or other networks 150). Memory 604 generally comprises a random-access memory ("RAM"), a read only memory ("ROM"), and a permanent mass storage device, such as a disk drive.

Memory 604 may contain one or more instances of web browsers 614, of local apps 624, or of operating systems 626. These and other software components may be loaded from a non-transitory computer readable storage medium 618 into memory 604 of the device 600 using a drive mechanism (not shown) associated with a non-transitory computer readable storage medium 618, such as a floppy disc, tape, DVD/CD-ROM drive, flash card, memory card, or the like. In some embodiments, software or other digital components may be loaded via the network interface 606, rather than via a computer readable storage medium 618. Special-purpose circuitry 622 may, in some variants, be configured to be worn by or otherwise configured to gather sensor data pertaining to behaviors and other attributes 453 of human subjects 105, 205, 305, 405. They may be used to explain visually or otherwise supplement a haptic message 298 in real time as described herein, such as to display a natural language descriptor (e.g. via a local app 625) corresponding to a currently- or recently-delivered notification to overcome a difficulty of a haptic notification 298 or symbol 329 being initially too cryptic for a new user. Moreover they may include one or more instances of antennae (not shown), of microphones 631, of kinematic sensors 632, of global position tracking sensors 633, or of other auxiliary sensors 634 (e.g. configured to acquire visual or other correlative indicia of one or more contextual attributes 453 for use as learning data by artificial intelligence or intelligence augmentation) as described herein. Alternatively or additionally, wearable or other instances of client device 600 may include some or all of the event-sequencing logic (e.g. for distillation or other edge processing) as described herein. In some embodiments device 600 may include many more components than those shown in FIG. 6, but it is not necessary that all conventional components of a client device 600 be shown in order to disclose an illustrative embodiment.

Figure 7:
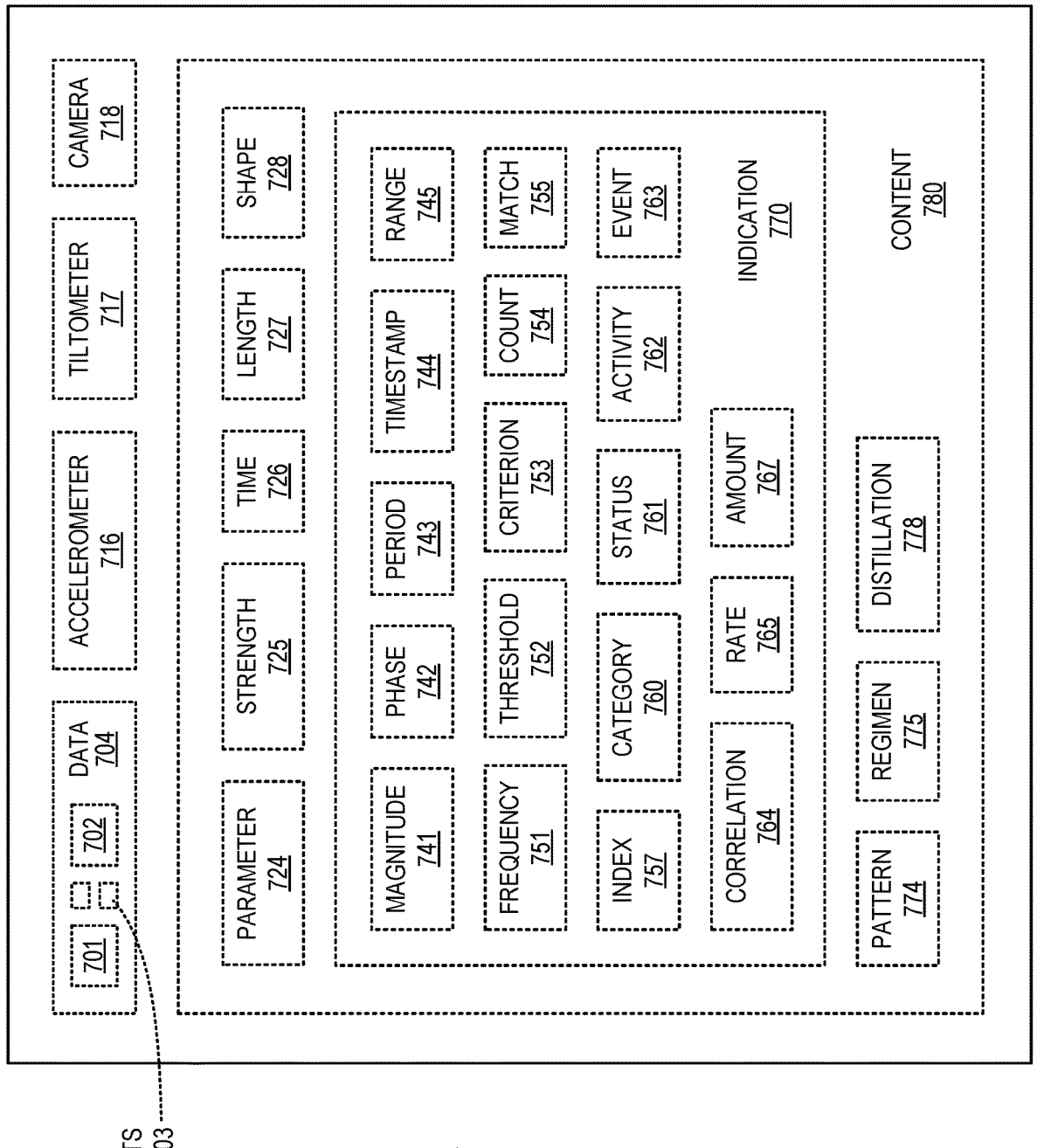
FIG. 7 depicts data-handling media with data sources, expressions, and related phenomena in which one or more improved technologies may be incorporated.

FIG. 7 schematically illustrates one or more distributed or other tangible data-handling media 700 comprising one or more instances of memories 504, 604; of special-purpose circuitry 522, 622; or of other hardware configured to handle data 704. Such hardware may include one or more idiothetic kinematic sensors 132, 232 such as accelerometers 716 or tiltometers 717 configured to provide position-, velocity- or acceleration-indicative signals or combinations of these as components 703 of sensor data 701, 702 described herein. Such media 700 can likewise include one or more instances of parameters 724, of strengths 725, of times 726, of lengths 727, of shapes 728, or of other such instances of indications 770, of patterns 774, of regimens 775, or of distillations 778. Alternatively or additionally such media 700 may contain one or more instances of magnitudes 741; of phases 742; of periods 743; of timestamps 744; of ranges 745; of frequencies 751; of thresholds 752; of criteria 753; of counts 754; of matches 755; of indices 757; of categories 760; of statuses 761; of activities 762; of events 763; of correlations 64, 764; of rates 765; of amounts 767; or of various other indications 770 pertaining to cohort data 60 or other event attributes 453 as described below.

Figure 8:
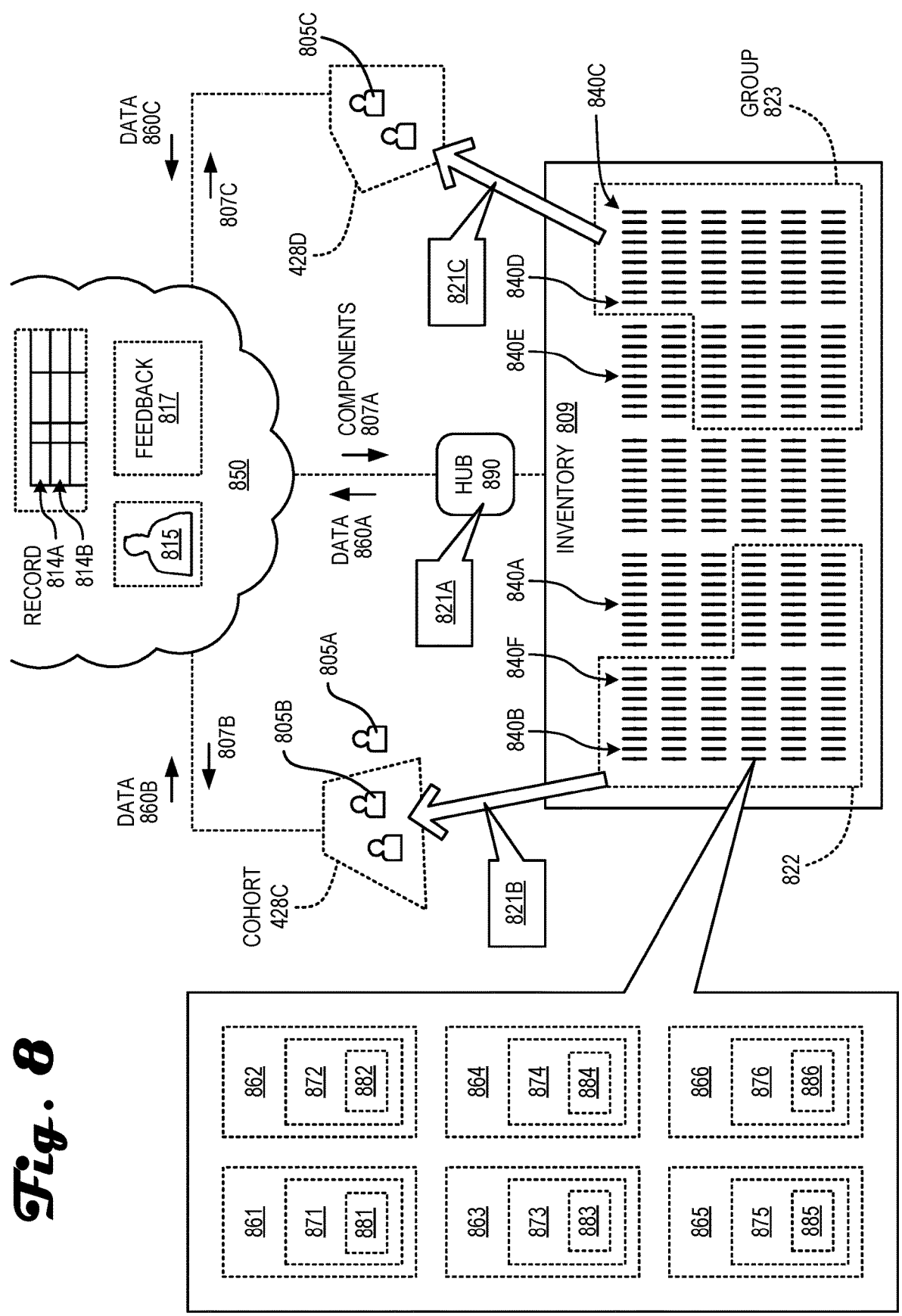
FIG. 8 illustrates how versioning groups of wearable articles may be facilitated in which one or more improved technologies may be incorporated.

FIG. 8 schematically illustrates another system 200 in which one or more technologies may be implemented, for example, for managing an inventory 808 of wearable articles 840 (e.g. smart watches) as they are deployed to various cohorts 428C-D of healthcare recipients or other human subjects 805. To ascertain appropriate establishment or adjustment so as to allow a first article 840A to function well one or more other articles 840B, 840F of a particular type (e.g. in group 822) are monitored while in use by one cohort 428C to the degree that each member of that cohort 428C registers a worn article 840 by sending at least a serial number or other unique article-identifying data 860B. In some contexts, for example, establishing a wireless linkage 288A between a mobile device 600B allows a newly purchased article 840B to identify itself and to synchronize current protocols 220 and operating parameters 224 with recommended recent updates (e.g. as update components 807B). Alternatively or additionally one or more other articles 840C, 840D of a newer type (e.g. in group 823) are monitored while in use by another cohort 428D that authorizes regularly uploaded performance data 860C and synchronizing with one or more alternative protocols 220 or operating parameters 224 or both (e.g. as update components 807C).

By arming one or more evaluators 815 with very numerous training data records 814A-B or distillations thereof, one or more such evaluators may manually or otherwise designate which differentiated protocol 220 among two or more is worthiest of adoption for undistributed remaining inventory such as wearable articles 840A, 840E. Likewise one or more such evaluators may manually or otherwise designate which differentiated (minimum or maximum value of a range 745 or other) operating parameter 224 among two or more is worthiest of proliferation into remaining inventory 808 such as wearable articles 840A, 840E or other open avenues for updates.

Some inventive variants herein relate to one or more first-type articles 840 including a first wearable article 840A and also to a group 822 of numerous second-type articles 840 that include a second wearable article 840B. In some contexts a hub 890 may be configured to manage a central or regional inventory 808 of articles 840 as shown, implementing vetted updates via one or more instances of deployment modules 268 that reside in one or more such networks 850 or in edge devices like hub 890 (or both). One or more such modules are configured to cause a first wearable article 840A to adopt or otherwise receive a particular rule 821A therein as a duplicate instance of a prior rule 821B that was previously established in (each of) the numerous second-type articles 840 of group 822 as a conditional response 287 based on one or more scalar indices 757 that each quantify an event count 754 or other amount 767 of use of at least the second wearable article 840B or of other articles 840F of the same type. One or more requirements 775 pertaining to an average, quartile, or other scalar distillation 778 of such amounts 767, for example, typically determine a corresponding threshold 752 by which a digital amount 767 of use of a particular wearable article 840B can determine whether that type of article was "successful" or not. If a count 754 of X haptic notifications 298 per month via actuator 238 exceeds an evaluator-assigned threshold 752 of 5 to 50 instances, for example, that is an example of a binary indication 770 of successful use. Likewise a corresponding threshold 752 may determine whether a number of days or meals or other such amounts 767 signaled a success of wearable article 840B serving its purpose or of a larger group 822 serving its purpose successfully. Moreover many such component thresholds 752 of success may be determined by one or more context- or article-specific protocols 220 or otherwise without comparison-specific opinion surveys or other implausible human interactions in light of teachings herein.

In some contexts one or more records 814 may be aggregated as field data 860 so as to reflect the rule 821B having triggered haptic notifications 298 via the second wearable article 840B and others like it each as a conditional response 287 to apparently suboptimal rates 765 of ingestion at each corresponding wearable article. That a measured rate 765 is suboptimal may be gleaned, for example, by imposing respective ranges 745 or thresholds 752 upon one or more corresponding limb motion or sound volume magnitudes 741, relative signal phases 742, signal periods 743, ingestion indicative timestamps 744, angular ranges 745, voice or vibration frequency 751, or other such data 704. Neural networks or other artificial intelligence modules as described herein may allow meaningful indications to be gleaned despite the relatively large noise that might be present in such data 704 provided that a sufficiently large set of training data records 814 are obtained. Success-indicative and other feedback 817 as described herein can provide suitable scoring functions for use in various machine learning applications, whether or not auxiliary data 294 are available to accelerate improvements in each sequential protocol 220A-C.

Such data 704 may form a basis, for example, by which (an instance of) a recognition module 862 can locally generate a fairly reliable local indication 770 that a wearer is apparently eating too fast for a corresponding consumption mode 297 in real time. Another can locally generate a fairly reliable local indication 770 that a wearer is apparently swallowing too soon or not chewing enough (or both) after taking each bite. Another can locally trigger a fairly reliable haptic notification 298 based upon a protocol 220 derived from upright-gripped beverage containers being handled infrequently enough to signal a suboptimally hydrated subject 205, 705. This can occur, for example, in a context in which too low of a rate 765 of drinking water is deemed suboptimal. But to avoid misinterpreting data 704 pertaining to a ping pong match, personal grooming, or other such non-ingestion-related activities 762 associated with limb oscillation, in some contexts a negative rule 821B may be effective for preventing a false positive haptic notification 298 (e.g. in which a haptic actuator 238 is energized in error).

Many haptic notifications 298 contemplated herein warn a wearer if problematic ingestion is likely enough but present no notification if data 704 seems indeterminate or if one or more targeted behavioral metrics (e.g. healthy rates 765 of ingestion or exercise) are apparently within respective favored ranges 745. Toward this end as used herein a positive indication of a suboptimal rate is "fairly reliable" if it is more than 60% likely to be right. And a negative indication of ingestion (e.g. one that indicates a lack of ingestion) is "fairly reliable" as used herein if it is more than 20% likely to be right. Likewise a negative indication of an ingestion rate problem (e.g. one that signals that a rate of ingestion is suboptimal) is "fairly reliable" as used herein if it is more than 20% likely to be right. It is expected that standards of what is "reliable enough" will drift from these values as protocols 220 improve over time, however, especially in light of machine learning technologies described herein. As used herein a "real time" transmission is one that occurs within less than thirty seconds after (a microphone or other sensor acquires) a last digital element of sensor data that affected the transmission.

Figure 9:
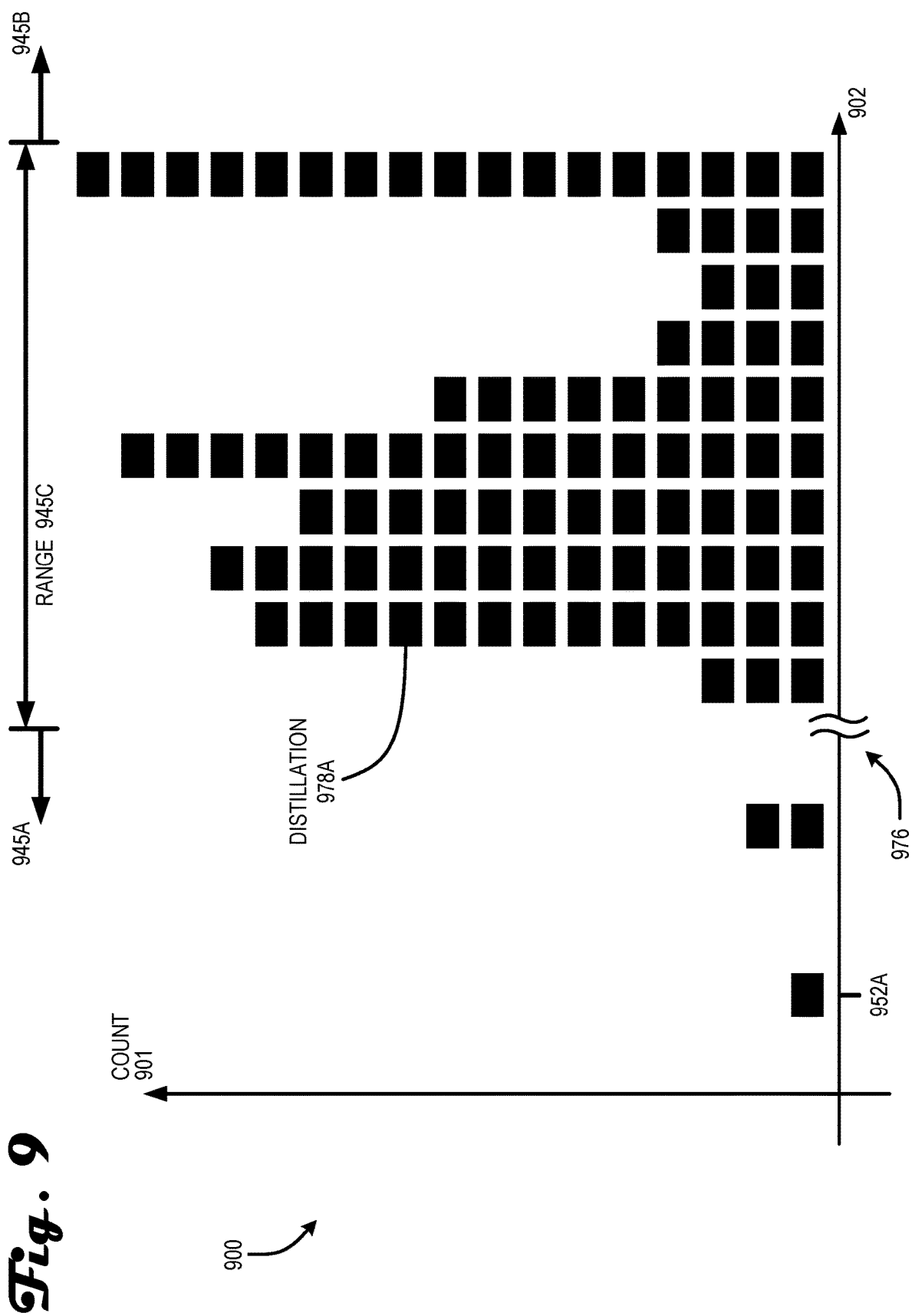
FIG. 9 illustrates a distribution of instructive empirical data across a single device type in which one or more improved technologies may be incorporated.

FIG. 9 depicts an extreme range 945A, a mainstream range 945B, and a marginal range 945C of hundreds of values 902 (or more) on the "low side" of a realistic bell-shaped distribution 900. A mean of the mainstream (or ideal/normal) range 945B is to the right of the depicted values 902, not shown. Each rectangle shown represents an empirical scalar aspect of a corresponding event 763 monitored by a second-type article 240, 840. Although a first-type wearable article 140 has fewer features than a corresponding second-type wearable article 240, first-type articles 140, 840 could likewise yield a monolithic distribution 900 like that of FIG. 9 because no contextual attributes 453 are used for defining wearer cohorts 428 or other context-specific event groupings of the distribution 900 as shown in FIG. 9.

To add meaning in a histogram like this, an evaluator 815 may conventionally characterize the distribution with explicitly provided ranges. Such ranges may be based, for example, on a user-provided number of standard deviations ("sigmas") below a mean value, for example, or on a user-specified confidence interval of 90% or 95%. A range 945C may be deemed "marginal" if it includes outcome values 902 of 2-3 sigmas below the mean value. Because the empirical values 902 from various event contexts 453 are jumbled together in this mixed distribution 900, such indicia of "spread" are larger than they might otherwise be. (The scales of counts 901 and values 902 are linear but the value spread of FIGS. 9-12 is mitigated with a gap 976 as shown.)

Figure 10:
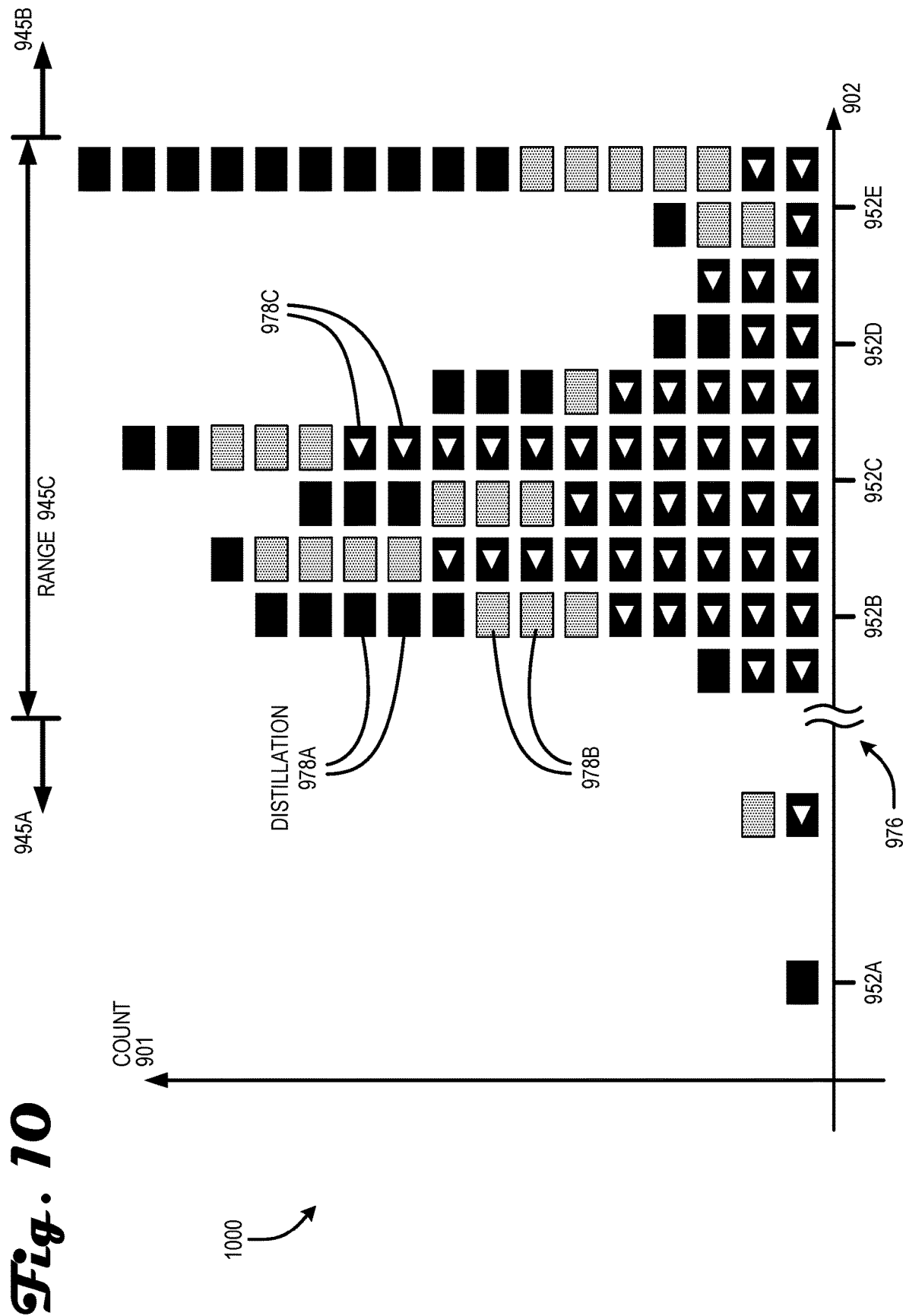
FIG. 10 illustrates the same data as FIG. 9 but also includes useful indicia about contextual partitioning in which one or more improved technologies may be incorporated.

FIG. 10 indicates the same events 763 as those of FIG. 9 but also signals one or more attributes 453 of many of the events 763. Such attributes are used for aggregating and partitioning them into cohorts 428 of several wearers, behaviors, or other elements of context shared among subsets of the events 763. As shown some distillations 978A of events defied classification and remain nondescript and unclassified. But in examining one or more distillations 978B pertaining to a first cohort 428 of wearers of second-type articles 240 that generated several marginal values 902 at the low end of an ideal range 945B of empirical values 902, a first evaluator 815 may study (wearer demographic, time-of-day, or other available metadata characterizing) such events 763 and determine that the first cohort 428 can be differentiated using primary data 701 even in lieu of context. This may occur in a context in which a set of such distillations 978 are defined by a characteristic pattern of tilt or movement (e.g. if the articles 840 have enabled suitable kinematic sensors 132, 232); of recognizable patterns 774 of uttered speech (e.g. common Spanish-language terms); or other such phenomena that may be recognized effectively using only a sensor configuration of a first-type article 140. In this fortuitous case the evaluator 815 may effectively subdivide two or more thresholds 752 so that one pertains to the particular context 427 and one or more others thresholds 752 pertain to other contexts. A lax threshold 952A-B may be deemed advantageous for a first cohort 428, for example, relative to a stricter threshold 952C-D applicable to wearers who are not in the first cohort 428. Likewise such bifurcation may be authorized in a context in which a first tilt change magnitude 741 can be differentiated reliably enough (i.e. with a strong enough negative or positive correlation 64) using attributes 453 detectable in primary data 701 or in which a first repetitive acceleration frequency 751 can be differentiated reliably enough using attributes 453 detectable in primary data 701 (or both in combination). Likewise such bifurcation may be authorized in a context in which a meaningful range 745, 945 of repetitive acceleration magnitude 741 or frequency 751 (or both) can be recognized reliably enough merely using attributes 453 detectable in primary data 701. Likewise (if the articles 240, 840 have enabled microphones 131, 231) such bifurcation may be authorized in a context in which a meaningful indication 770 that a first recognizable (linguistic, loudness, handling dishes, or other matchable) audible pattern 774 can be recognized reliably enough merely using attributes 453 detectable in primary data 701. Likewise such bifurcation may be authorized in response to an indication 770 that a lunchtime or similar time-of-day indication 770 of a detectable activity 762 (e.g. eating) or other recognizable pattern 774 recognized reliably enough merely using attributes 453 detectable in primary data 701.

Figure 11:
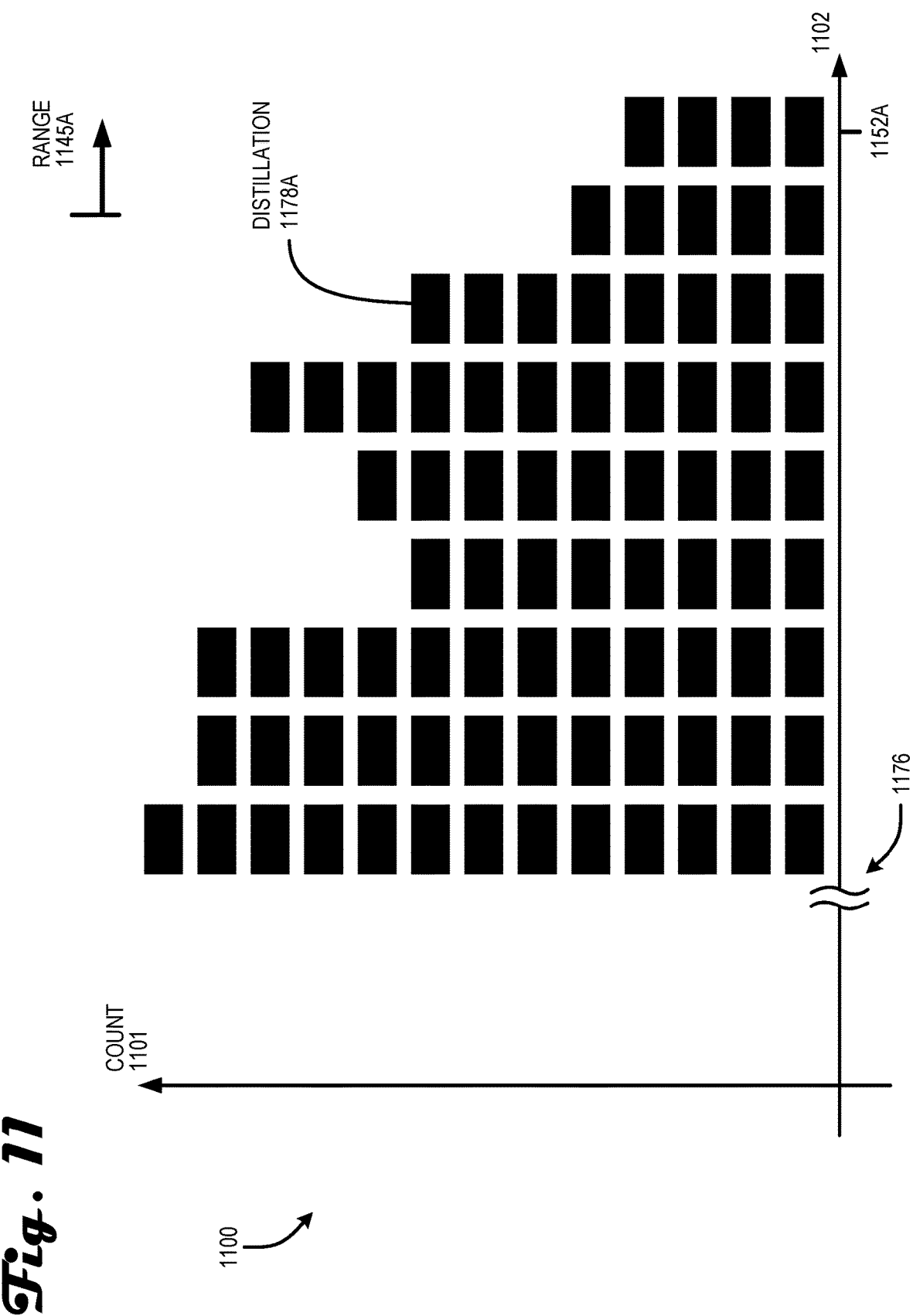
FIG. 11 illustrates another distribution of instructive empirical data across a single device type in which one or more improved technologies may be incorporated.

FIG. 11 depicts an extreme range 1145A pertaining to a distribution 900, 1100 of hundreds or more measured, computed, or other realistic values 1102 on the "high side" of a histogram distribution 1100. A mean of the mainstream range is (in gap 1176) not shown. Each rectangle shown represents an empirical scalar aspect of a corresponding event 763 monitored by a second-type article 240, 840. Although a first-type article 140, 840 has fewer features than a corresponding second-type wearable article 240, could likewise yield a monolithic distribution 1100 like that of FIG. 11 because no contextual attributes 453 are used for defining wearer cohorts 428 or other context-specific event groupings of the distribution 1100 as shown in FIG. 11. Because the empirical values 1102 from various event contexts 453 are jumbled together in this mixed distribution 1100, such indicia of "spread" are again expected to be larger than that of a more uniform event context 427 or cohort 428.

Figure 12:
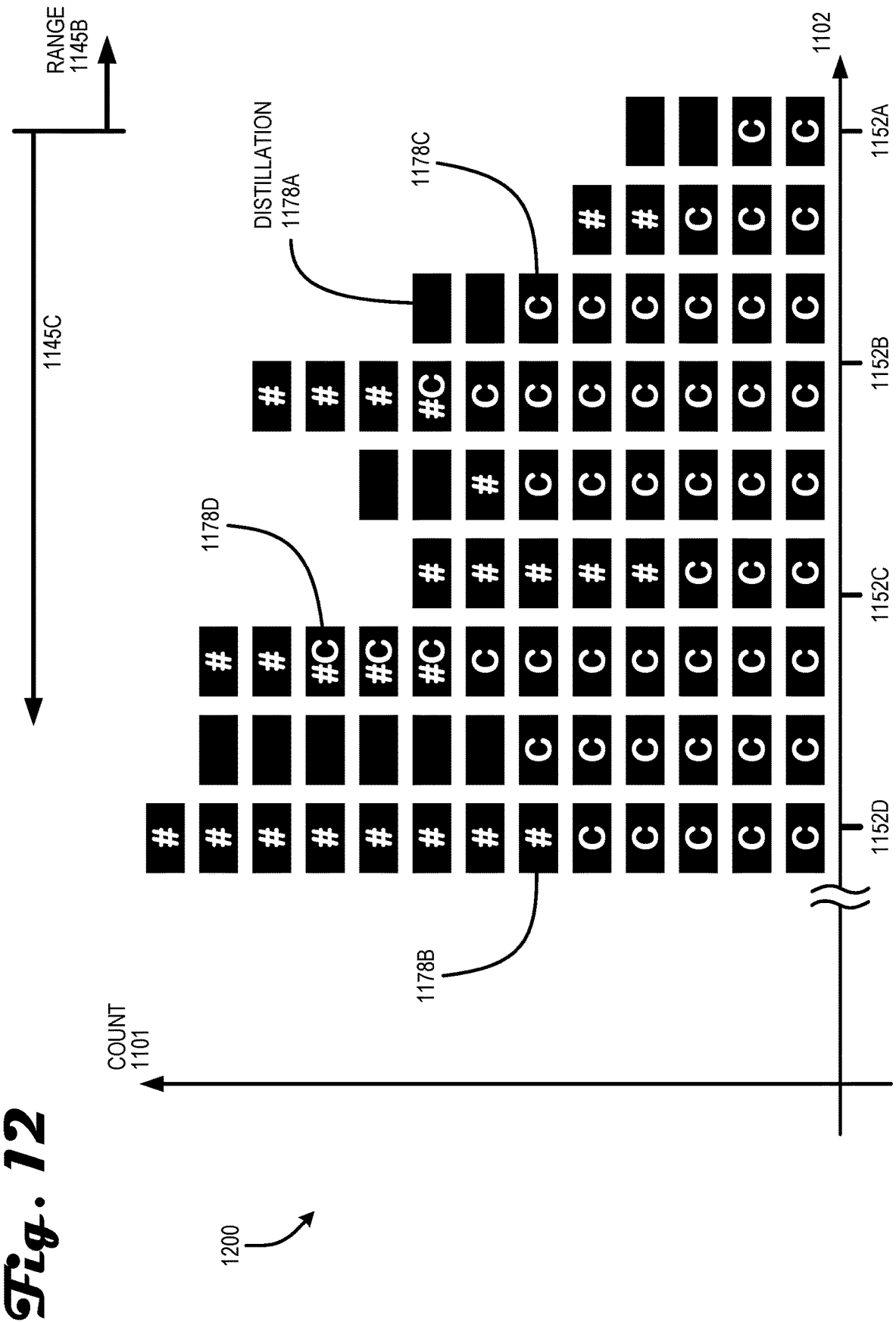
FIG. 12 illustrates the same data as FIG. 11 but also includes useful indicia about contextual partitioning in which one or more improved technologies may be incorporated.

FIG. 12 indicates the same events 763 as those of FIG. 11 but also provides metadata pertaining to one or more attributes 453 of most of those events. Event attributes 453 are used for aggregating and partitioning them along the same lines as those of FIG. 9. Rather than transmitting a query 286 to a human user this time a range-bounding or operating threshold 752 is obtained automatically as a conventional distillation 1178A (e.g. a percentile or maximum value 1152A). In a range 1145B above this threshold 752 any empirical value 1102 encountered is treated as "extreme." In a range 1145C below this threshold an empirical value 1102 is deemed "eligible" for use as a reminder-triggering or other useful threshold as further described below.

As shown some distillations 1178A of events 763 again defied classification and remain unclassified. But in examining context-enriched distillation 1178B pertaining to a second-type event context 427 that generated numerous marginal values 1102 at the high end of an ideal range 945B, an insightful evaluator 815 may study (photographic or other available metadata characterizing) such events 763 and determine that such contexts 427 are not (yet) readily distinguishable. The insightful evaluator 815 may then try to find ways to use primary data 701 to subdivide the thresholds 752 pertaining to such events 763 according to wearer demographic or other potentially available criteria 753. And in the meantime the insightful evaluator 815 may use her knowledge of second-type event contexts 427 and an apparently or actually worst-case cohort 428 to predict that future members thereof would appreciate a haptic reminder notification 298 (a) frequently, perhaps a few times a week; (b) rarely, perhaps not even once a month; or perhaps (c) at least monthly but at most twice a week. Even without numerous events 763 upon which to base precise thresholds 752, such coarse insight might allow such an evaluator 815 to implement correspondingly (a) aggressive haptic notifications 298 using stricter threshold values 952D, 1152D; (b) rare haptic notifications 298 using relaxed threshold values 952A-B, 1152A-B; or (c) intermediately intrusive haptic notifications 298 using threshold values 952C, 1152C. This can occur, for example, in a context in which differently-aggressive thresholds 752 at each end of a distribution 900, 1100 are tailored to completely different demographic or other contexts 427; in which thresholds 752 at both ends would otherwise give false negatives by virtue of diverse contexts 453 treated with crude analysis of jumbled-together mixed distributions 1100; and in which such confusion would otherwise lead quickly to frequent battery discharge and other irritations resulting from inappropriate haptic notifications 298. In some variants, moreover, other distillations 1178C as shown likewise allow for separate consideration and distinct treatment, notwithstanding a recognition of one or more overlap distillations 1178D as a subclass of each component.

Figure 13:
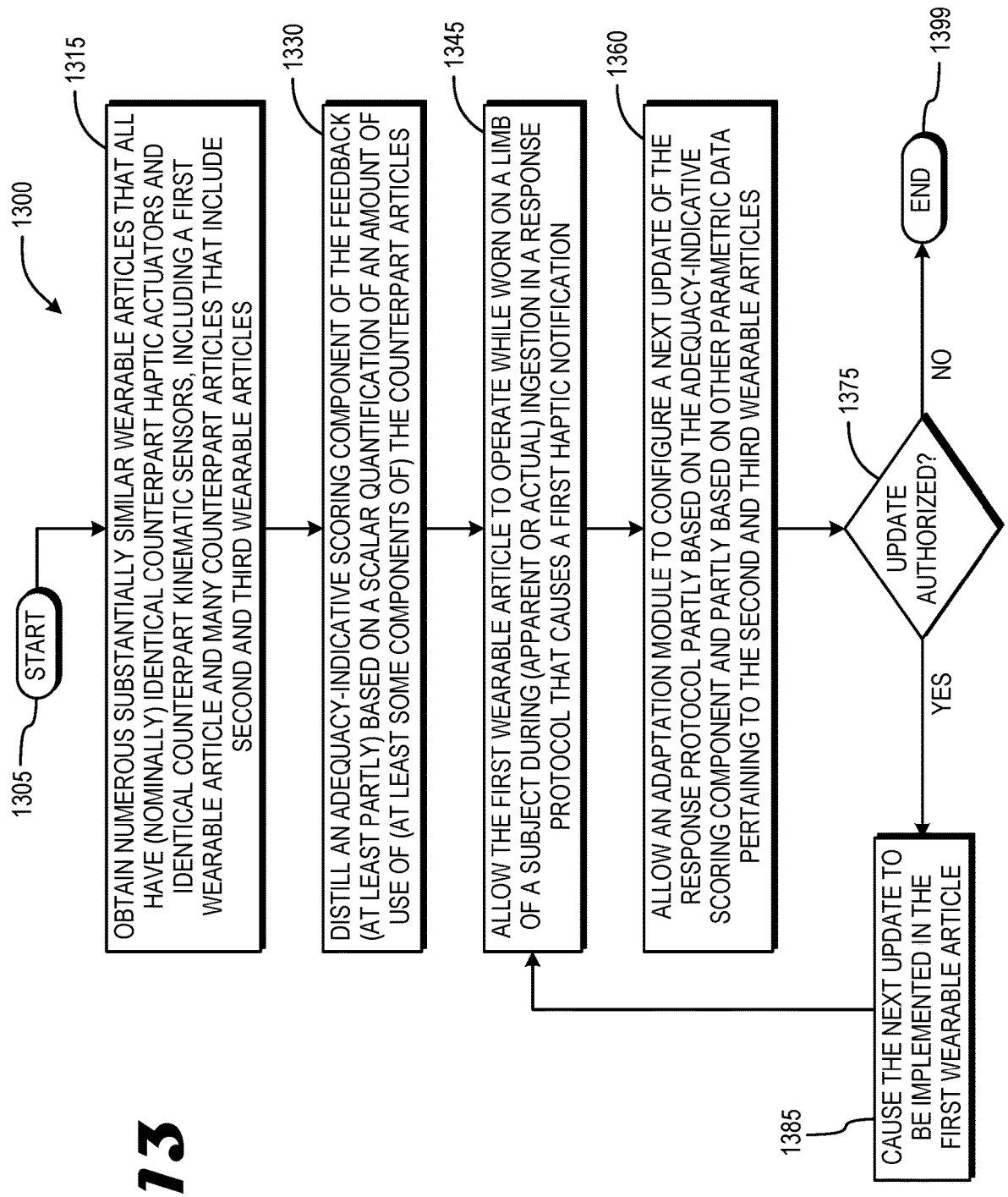
FIG. 13 depicts an operational flow in which wearable articles are updated according to one or more improved technologies.

FIG. 13 illustrates an operational flow 1300 suitable for use with at least one embodiment, such as may be performed on a server 500 or client device 600 (or both) using special-purpose circuitry 522, 622 thereof. As will be recognized by those having ordinary skill in the art, not all events of information management are illustrated in FIG. 13. Rather, for clarity, only those steps reasonably relevant to describing the helpful interaction aspects of flow 1300 are shown and described. Those having ordinary skill in the art will also recognize the present embodiments are each merely one exemplary embodiment and that variations thereof may be made without departing from the scope of the broader inventive concept set forth in the clauses and claims below.

Operation 1305 depicts a start operation.

Operation 1315 describes (configuring or otherwise) obtaining numerous substantially similar wearable articles that all have (nominally) identical counterpart haptic actuators and identical counterpart kinematic sensors, including a first wearable article and many counterpart articles that include second and third wearable articles (e.g. by a configuration module 262 at a factory or by someone who acquires the articles).

Operation 1330 describes distilling an adequacy-indicative scoring component of the feedback (at least partly) based on a scalar quantification of an amount of use of (at least some components of) the counterpart articles (e.g. by a distillation module 263, for example, residing in one or more servers 500). In some variants, for example, whether one or more events 763 are included in a count 754 or affect some other distillation 778, 978, 1178 depends upon whether one or more measurements or other empirical values 902, 1102 derived from sensor data 702 from the event 763 reaches a corresponding extended or other qualifying threshold 752, 952, 1152 as further described below. In some variants such a threshold may be selected by, received from, or otherwise authorized by a suitable entity such as one or more learning modules 267 or one or more human evaluators 815. In some contexts such operational parameters may be obtained using a supervised learning module 267 or other intelligence amplification circuitry 222 (or both). Alternatively or additionally a protocol for adopting such rules 821 may include a structured dialog or other interface protocol 220 making suitable use of one or more pairings of query 286 and response 287 in light of teachings herein.

Operation 1345 describes allowing the first wearable article to operate while worn on a limb of a subject during (apparent or actual) ingestion in a response protocol that causes a first haptic notification (e.g. by an instance of an authorization module 264).

Operation 1360 describes allowing an adaptation module to configure a next update of the response protocol partly based on the adequacy-indicative scoring component and partly based on other parametric data pertaining to the second and third wearable articles (e.g. by a recognition module 266 and configuration module 262 operating jointly).

Operation 1375 indicates a determination whether or not the update is authorized (e.g. by a control module 265). If so flow passes to operation 1385, otherwise control terminates at operation 1399.

Operation 1385 describes causing the next update to be implemented in the first article (e.g. by a deployment module 268).

FIG. 14 illustrates an operational flow 1400 suitable for use with at least one embodiment, such as may be performed on a wearable client device 600 using special-purpose circuitry 622 thereof. As will be recognized by those having ordinary skill in the art, not all events of information management are illustrated in FIG. 14. Rather, for clarity, only those steps reasonably relevant to describing the helpful aspects of flow 1400 are shown and described. Those having ordinary skill in the art will also recognize the present embodiments are each merely one exemplary embodiment and that variations thereof may be made without departing from the scope of the broader inventive concept set forth in the clauses and claims below.

Operation 1405 describes a start operation.

Operation 1410 describes comparing one or more ingestion-predictive patterns with local data in a low-energy operating mode (e.g. by a first recognition module 862 aboard each wearable article in a particular group 822 or inventory 808 of such articles comparing sensor data 701, 702 aboard a wearable article 840 against one or more criteria 753 coarsely indicative of eating-arm motions or chewing/slurping noises symptomatic of eating or drinking and signaling a match 755 if satisfied or an absence thereof if not). This can occur, for example, in a context in which counterpart sensor data 701, 702 aboard similarly configured prior second-type articles 240, 840B have been used to tailor the one or more criteria 753 to correspond with eating-arm motions or chewing/slurping noises seen or heard by one or more crowdsourced or other evaluators 815 observing auxiliary data 294 pertaining to subjects 205, 805B in a sufficiently-large cohort 428C. In some contexts, for example, prototype articles 840F can be used by one or more evaluators 815 serving as human subjects 205 so as to provide "seed" data 860B that exemplifies such eating-arm motion patterns 774 or chewing/slurping noise patterns 774 as they are manifested in prototype trial data 860B through a particular configuration of microphones 231, accelerometers 716, tiltometers 717, or other such sensors 232, 233 some or all of which are matched with counterpart sensors in the first-type article(s) 140A; and in which adjustments to one or more thresholds 752 that characterize/bound such patterns 774 are thereafter improved by successive iterations of protocols 220. Flow then passes to operation 1415.

Operation 1415 indicates obtaining a determination whether or not an ingestion event is indicated (e.g. by a control module 864 aboard the same wearable article 840 obtaining the determination as an outcome of the above-described match 755). If not flow passes to operation 1410, otherwise flow passes to operation 1420.

Operation 1420 describes comparing one or more healthy-ingestion-contraindicative patterns with local data in a high-energy operating mode (e.g. by a second recognition module 862 aboard the same wearable article 840). Flow then passes to operation 1435.

Operation 1435 indicates obtaining a determination whether or not an ingestion event is still indicated (e.g. by another instance of a control module 864 aboard the same wearable article 840). If not flow passes to operation 1410, otherwise flow passes to operation 1465.

Operation 1465 indicates obtaining a determination whether or not the event signals an unhealthy or other suboptimal eating or other behavior (e.g. by another instance of a control module 864 aboard the same wearable article 840 that has crowdsourced or other heuristically determined parameters that designate what behavior is "suboptimal"). If so flow passes to operation 1470, otherwise flow passes to an end operation 1499.

Operation 1470 describes initiating a first haptic notification based on first sensor data on a first wearable article signaling that an occurrence count of first-type events (e.g. seconds per mouthful/bite/delivery or other matched pattern 774) detected via the first wearable article has reached a first occurrence count threshold (e.g. by a response module 863 and invocation module 866 functioning aboard the same wearable article 840 operating jointly). Flow then passes to operation 1480.

Operation 1480 describes automatically and conditionally extending the first haptic notification based on first sensor data on the first wearable article indicating a suboptimal rate of consumption delivered using a first response protocol (e.g. by another instance of a control module 864 aboard the same wearable article 840). Flow then passes to operation 1495.

Operation 1495 describes automatically and conditionally discontinuing the first haptic notification based on additional sensor data on the first wearable article indicating that the suboptimal rate of consumption has not continued (e.g. by one or more other modules aboard the same wearable article 840). Flow then passes to an end operation 1499. This can occur, for example, in a context in which another iteration starting at operation 1405 would commence after an energy-saving programmatic delay of more than an hour.

In light of teachings herein, numerous existing techniques may be applied for configuring special-purpose circuitry or other structures effective for correlating, distilling, recognizing, recording, facilitating, and other operations as described herein without undue experimentation. See, e.g., U.S. patent Ser. No. 10/790,054 ("Method and apparatus for tracking of food intake and other behaviors and providing relevant feedback"); U.S. patent Ser. No. 10/772,559 ("Wearable food consumption monitor"); U.S. patent Ser. No. 10/627,861 ("Wearable device for the arm with close-fitting biometric sensors"); U.S. patent Ser. No. 10/458,845 ("Mobile device for food identification and quantification using spectroscopy and imaging"); U.S. patent Ser. No. 10/429,888 ("Wearable computer display devices for the forearm, wrist, and/or hand"); U.S. patent Ser. No. 10/321,873 ("Smart clothing for ambulatory human motion capture"); U.S. patent Ser. No. 10/234,942 ("Wearable and mobile brain computer interface (BCI) device and method"); U.S. patent Ser. No. 10/234,934 ("Sensor array spanning multiple radial quadrants to measure body joint movement"); U.S. patent Ser. No. 10/130,277 ("Willpower glasses (TM)—a wearable food consumption monitor"); U.S. Pat. No. 9,582,035 ("Wearable computing devices and methods for the wrist and/or forearm"); U.S. Pat. No. 9,568,492 ("Fitness monitoring device with altimeter and gesture recognition"); U.S. Pat. No. 9,529,385 ("Smart watch and human-to-computer interface for monitoring food consumption"); U.S. Pat. No. 9,067,070 ("Dysgeusia-inducing neurostimulation for modifying consumption of a selected nutrient type"); U.S. Pat. No. 9,049,998 ("Biometric monitoring device with heart rate measurement activated by a single user-gesture"); U.S. Pat. No. 9,254,099 ("Smart watch and food-imaging member for monitoring food consumption"); U.S. Pub. No. 20200164209 ("Systems and methods for using a transcutaneous electrical stimulation device to deliver titrated therapy"); U.S. Pub. No. 20200152312 ("Systems for nutritional monitoring and management"); and U.S. Pub. No. 20140274078 ("Protocols for facilitating broader access in wireless communications").

While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

In the numbered clauses below, all of the words and phrases used will be understood to one of ordinary skill as being either a natural language expression with a plain meaning or a term of art to be construed in light of statements herein. First combinations of aspects and embodiments are articulated in a shorthand form such that (1) according to respective embodiments, for each instance in which a "component" or other such identifiers appear to be introduced (e.g., with "a" or "an,") more than once in a given chain of clauses, such designations may either identify the same entity or distinct entities; and (2) what might be called "dependent" clauses below may or may not incorporate, in respective embodiments, the features of "independent" clauses to which they refer or other features described above.

CLAUSES

1. A haptic feedback support method relating to one or more first-type articles 840 including a (particular) first wearable article 140, 840A and also relating to one or more second-type articles 840 that include a first set (e.g. group 822) of one or more second-type articles 840 of the one or more second-type articles 840, wherein the first set includes at least a second wearable article 240, 840B and wherein the method comprises:

invoking transistor-based circuitry (e.g. a deployment module 268 in a hub 890 that manages a central or regional inventory 809 of articles) configured to cause the first wearable article 140, 340A, 840A (e.g. via hub 890 as shown in FIG. 8) to receive a particular rule 321A, 821A therein as a duplicate instance of a prior rule 821B previously established in (each of) the one or more second-type articles 840 as a conditional response 287 (at least partly) based on a first quantified index 757 of a heuristically determined percentage or other amount 767 of use of the first set of the one or more second-type articles 840 (crossing or otherwise) reaching a threshold 752 (e.g. in hours or counted occurrences of an event) including allowing the prior rule 821B to trigger a haptic notification 298 via second wearable article 240, 840B as a conditional response 287 to an indication 770 of a first rate 765 (e.g. relating to suboptimal ingestion or other human activity); and invoking transistor-based circuitry (e.g. a control module 265 and an authorization module 264 jointly) configured to allow the first wearable article 140, 340A, 840A to invoke the particular rule 321A, 821A so as to trigger a haptic notification 298 via the first wearable article 140, 340A, 840A as a conditional response 287 to an indication 770 of a rate 765 (e.g. relating to ingestion or other human activity) in the first wearable article 140, 340A, 840A wherein the haptic notification 298 via the first wearable article 140, 340A, 840A is implemented by powering a first actuator 138 of the first wearable article 140, 340A, 840A.

2. A haptic feedback support method relating to one or more first-type articles 840 including a first wearable article 140, 840A and also relating to one or more second-type articles 840 that include a first set (e.g. group 822) of one or more second-type articles 840 of the one or more second-type articles 840, wherein the first set includes at least a (particular) second wearable article 240, 840B and wherein the method comprises:

invoking transistor-based circuitry (e.g. a deployment module 268 in a hub 890 that manages a central or regional inventory 809 of articles) configured to cause the first wearable article 140, 340A, 840A (e.g. via hub 890 as shown in FIG. 8) to receive a particular rule 321A, 821A therein as a duplicate instance of a prior rule 821B previously established in (each of) the one or more second-type articles 840 after transmitting a first quantified index 757 of or other (average or sampling or other) distillation 778 of a heuristically determined percentage or other amount 767 of use of the first set of the one or more second-type articles 840 to one or more evaluators 815 and thereafter receiving from (at least one of) the one or more evaluators 815 an authorization (e.g. as an update component 807A therewith) to implement the particular rule 321A, 821A therein as the duplicate instance of the prior rule 821B previously established in (each of) the one or more second-type articles 840 including allowing the prior rule 821B to trigger a haptic notification 298 via the second wearable article 240, 840B as a conditional response 287 to an indication 770 of a first suboptimal rate 765 of ingestion; and invoking transistor-based circuitry (e.g. a control module 265 and an authorization module 264 jointly) configured to allow the first wearable article 140, 340A, 840A to invoke the particular rule 321A, 821A so as to trigger a haptic notification 298 via the first wearable article 140, 340A, 840A as a conditional response 287 to an indication 770 of a rate 765 (e.g. relating to ingestion or other human activity) in the first wearable article 140, 340A, 840A wherein the haptic notification 298 via the first wearable article 140, 340A, 840A is implemented by powering a first actuator 138 of the first wearable article 140, 340A, 840A.

3. A haptic feedback support method relating to one or more first-type articles 840 including a first wearable article 140 and also relating to one or more second-type articles 840 including a second wearable article 240, wherein the method comprises:

invoking transistor-based circuitry (e.g. control and invocation modules 864, 866 jointly) configured to initiate a first haptic notification 298 (at least partly) based on (one or more kinematic or other components 703 of) first sensor data 701 via the first wearable article 140 signaling a suboptimal ingestion (or other rate 765) or other behavior directly or otherwise detected via the first wearable article 140 using a first threshold 752.

4. A haptic feedback support method relating to one or more first-type articles 840 including a first wearable article 140 and also relating to one or more second-type articles 840 including a second wearable article 240, wherein the method comprises:

invoking transistor-based circuitry (e.g. control and invocation modules 864, 866 jointly) configured to initiate a first haptic notification 298 (at least partly) based on first sensor data 701 via the first wearable article 140 signaling (at least) a first (Boolean or other) explicit indication 770 of suboptimal first-type events 763 (e.g. too many or too few instances of a pattern match 755) using an occurrence count threshold 752.

5. The method of ANY one of the above clauses wherein whether one or more (actual or apparent) events 763 are included in a count 754 or other distillation 778, 978, 1178 depends upon whether one or more measurements, scores, differences, percentiles, distributions, or other empirical values derived from sensor data 702 from the event 763 reaches a corresponding qualifying threshold 752 received from a corresponding entity (e.g. one or more learning modules 267 or evaluators 815 engaged via a structured dialog or other interface protocol 220).

6. The method of ANY one of the above clauses wherein whether one or more (actual or apparent) events 763 are included in a count 754 or other distillation 778, 978, 1178 depends upon whether computed scalar amount 767 derived from sensor data 702 from the event 763 reaches a corresponding qualifying threshold 752 received from a corresponding entity (e.g. one or more learning modules 267 or evaluators 815 engaged via a structured dialog or other interface protocol 220).

7. The method of ANY one of the above clauses wherein whether one or more (actual or apparent) events 763 are included in a count 754 or other distillation 778, 978, 1178 depends upon whether computed scalar amount 767 derived from sensor data 702 from the event 763 reaches a corresponding qualifying threshold 752 or otherwise matches a pattern 774 of one or more qualifying criteria 753 derived from interactions with a corresponding entity (e.g. one or more evaluators 815 engaged via a structured dialog or other protocol 220).

8. The method of ANY one of the above clauses wherein determining whether one or more counts 754 or other distillations 778, 978, 1178 of similar-type events 763 derived from sensor data 702 (e.g. involving numerous same-type articles 840) thereof reaches a corresponding qualifying threshold 752 includes presenting several candidate threshold values 952, 1152 each generated as a (percentile, confidence interval, or other) conventional statistical protocol 220 to a corresponding entity (e.g. one or more learning modules 267) authorized to disqualify one or more inferior ones of the several candidate threshold values 952, 1152.

9. The method of ANY one of the above clauses wherein determining whether one or more counts 754 or other distillations 778, 978, 1178 of similar-type events 763 derived from sensor data 702 (e.g. involving numerous same-type articles 840) thereof reaches a corresponding qualifying threshold 752 includes presenting several candidate threshold values 952, 1152 each generated as a (percentile, confidence interval, or other) conventional statistical protocol 220 to a corresponding entity (e.g. one or more human evaluators 815) authorized to select one or more most preferred ones of the several candidate threshold values 952, 1152.

10. The method of ANY one of the above clauses wherein determining one or more qualifying thresholds 752 as described herein comprises identifying a decile, percentile or other most extreme eligible value 952A, 1152A as bounding or falling into an undesirably extreme range 945A, 1145A and comparing same against one or more less extreme eligible values 952B-D, 1152B-D distributed across an eligible distribution 900, 1100 (e.g. to estimate how common false positives and false negatives would be for each context 427 under scrutiny at each candidate threshold 752 under consideration).

11. The method of ANY one of the above clauses wherein determining one or more qualifying thresholds 752 as described herein comprises identifying a tercile, median, or other least extreme eligible value 952E, 1152D as bounding an ideal range 945B or spanning a broad marginal or eligible range 945C, 1145C and comparing same against some more extreme eligible values 952B-D, 1152A-C distributed across an eligible distribution 900, 1100 (e.g. to estimate how successful each candidate threshold 752 under consideration would be among wearers in a given cohort 428 who want haptic notifications 298).

12. The method of ANY one of the above clauses wherein at least one context-indicative sensor 234A used with each of second-type articles 240, 840 is aboard said second wearable article 240.

13. The method of ANY one of the above clauses wherein at least one context-indicative sensor 234 used with each of second-type articles 240, 840 is in a mobile device 600B with a direct wireless linkage 288A to said second wearable article 240 rather than being aboard said second wearable article 240.

14. The method of ANY one of the above clauses wherein at least one context-indicative sensor 234B used with each of second-type articles 240, 840 is aboard another wearable article 240 worn simultaneously on another body part of a wearer of the second wearable article 240 rather than being aboard said second wearable article 240.

15. The method of ANY one of the above clauses wherein at least one context-indicative sensor 234B used with each of second-type articles 240, 840 is aboard another wearable article 240 worn on another limb 208B rather than being aboard said second wearable article 240.

16. The method of ANY one of the above clauses wherein at least one context-indicative sensor 234B used with each of second-type articles 240, 840 is aboard another wearable article 240B directly or otherwise operably coupled (e.g. through one or more wireless linkages 288) to said second wearable article 240 rather than being aboard said second wearable article 240.

17. The method of ANY one of the above clauses wherein at least one context-indicative sensor 234 used with each of second-type articles 240, 840 is a camera 718 (attached to, integral to, or otherwise) aboard an other wearable article 240 rather than being aboard said second wearable article 240.

18. The method of ANY one of the above clauses wherein at least one context-indicative sensor 234 used with each of second-type articles 240, 840 includes a pedometer in a mobile device 600B with a direct wireless linkage 288A to said second wearable article 240 rather than being aboard said second wearable article 240.

19. The method of ANY one of the above clauses wherein at least one context-indicative sensor 234 used with each of second-type articles 240, 840 includes one or more accelerometers 716 in a mobile device 600B with a direct wireless linkage 288A to said second wearable article 240 rather than being aboard said second wearable article 240.

20. The method of ANY one of the above clauses wherein at least one auxiliary sensor 234 used with each of second-type articles 240, 840 comprises a Global Positioning System configured to provide positional auxiliary data 294 as a population-density-indicative or other geographic attribute 453 in association with one or more particular events 763 (or values 902, 1102 thereof) described herein.

21. The method of ANY one of the above clauses wherein at least one context-indicative sensor 234 used with each of second-type articles 240, 840 comprises a Global Positioning System in a mobile device 600B with a direct wireless linkage 288A to said second wearable article 240 rather than being aboard said second wearable article 240.

22. The method of ANY one of the above clauses wherein at least one context-indicative sensor 234 used with (at least) the second wearable article 240 is a first accelerometer 716, wherein no accelerometer is ever aboard the first wearable article 140, and wherein one or more evaluators 815 glean one or more attributes 453 of a context 427 that pertains to (a monitored event, wearer demographic, angular position, oscillation, or other aspect of) one or more second-type articles 240, 840 using data 702 from one or more such accelerometers 716.

23. The method of ANY one of the above clauses wherein at least one context-indicative sensor 234 used with (at least) the second wearable article 240 is a first tiltometer 717, wherein no tiltometer is ever aboard the first wearable article 140, and wherein one or more evaluators 815 glean one or more attributes 453 of a context 427 that pertains to one or more second-type wearable articles 240, 840 using data 702 from one or more such tiltometers 717.

24. The method of ANY one of the above clauses wherein at least one context-indicative sensor 234 used with (at least) the second wearable article 240 is a first camera 718, wherein no camera is ever aboard the first wearable article 140, and wherein one or more evaluators 815 glean one or more attributes 453 of a context 427 that pertains to (a monitored event, wearer demographic, angular position, oscillation, or other aspect of) one or more second-type wearable articles 240, 840 using data 702 from one or more such cameras 718.

25. The method of ANY one of the above clauses comprising:
    subdividing first and second thresholds 752 for use in first and second respective contexts 427, each in lieu of the other, in response to an indication 770 that a first tilt change magnitude 741 can be differentiated (e.g. by a strong-enough positive correlation 64, greater than 0.7, or a strong-enough negative correlation 64, less than −0.7) using attributes 453 detectable in primary data 701.

26. The method of ANY one of the above clauses comprising:
    subdividing first and second thresholds 752 for use in first and second respective contexts 427, each in lieu of the other, in response to an indication 770 that a lunchtime or similar time-of-day indication 770 of a detectable activity 762 (e.g. eating) or other recognizable pattern 774 can be differentiated using attributes 453 detectable in primary data 701.

27. The method of ANY one of the above clauses comprising:
    subdividing first and second thresholds 752 for use in first and second respective contexts 427, each in lieu of the other, in response to an indication 770 that a first repetitive acceleration frequency 751 can be differentiated using attributes 453 detectable in primary data 701.

28. The method of ANY one of the above clauses comprising:
    subdividing first and second thresholds 752 for use in first and second respective contexts 427, each in lieu of the other, in response to an indication 770 that a first repetitive acceleration magnitude 741 can be differentiated using attributes 453 detectable in primary data 701.

29. The method of ANY one of the above clauses comprising:
    subdividing first and second thresholds 752 for use in first and second respective contexts 427, each in lieu of the other, in response to an indication 770 that a first recognizable (linguistic, loudness, or other) audible pattern 774 can be differentiated using attributes 453 detectable in primary data 701.

30. The method of ANY one of the above clauses comprising:
    subdividing first and second thresholds 752 for use in first and second respective contexts 427, each in lieu of the other, in response to an indication 770 that a first cohort 428 can be differentiated (e.g. by a strong-enough positive correlation 64, greater than 0.7, or a strong-enough negative correlation 64, less than −0.7) using attributes 453 detectable in primary data 701.

31. The method of ANY one of the above clauses wherein one or more evaluators 815 or other such entities authorized one or more protocols 120, 220 or operating parameters 124, 224 after receiving a transmission 39 of one or more (distillations 778 of raw or other) rate-indicative values 902, 1102 or of other relevant event-descriptive data 294 (e.g. timestamps 744) pertaining to numerous events 763 that were captured by or otherwise involved second-type articles 240, 840.

32. The method of ANY one of the above clauses wherein one or more evaluators 815 or other such entities authorized one or more protocols 120, 220 or operating parameters 124, 224 after receiving a transmission 39 of one or more distillations 778 of rate-indicative values 902, 1102 or of other context-specific data 294 pertaining to numerous same-type events 763 that were captured by or otherwise involved numerous second-type articles 240, 840 including said second wearable article 240, 840.

33. The method of ANY one of the above clauses wherein a selective inclusion partition implements a first attribute 453 established by one or more event-type categories 760 confirmed by (a sufficient fraction of) several evaluators 815 who previously received context-indicative data 294 (at least some of which was) from a context-indicative sensor 234 used with said second wearable article 240 as a component of a data distillation 978, 1178 of a distribution 900, 1100 of second-type articles 240, 840.

34. The method of ANY one of the above clauses wherein at least one corporate or other entity that received event-descriptive data 294 as described herein includes (a sufficient consensus among) several crowdworkers who thereafter assign or confirm one or more categories 760 or other attributes 453 as metadata distillations 778, 978, 1178 pertaining to each event 763 in which a pattern 774 is recognized.

35. The method of ANY one of the above clauses wherein a selective inclusion partition implements an oscillation-related attribute 453 established by one or more (alphanumerically described or other) event-type categories 760 confirmed by one or more decision-making entities that previously received context-indicative data 294 from a context-indicative sensor 234 aboard or otherwise used with said second wearable article 240 as a component of a data distillation 978, 1178 of a distribution 900, 1100 of second-type articles 240, 840.

36. The method of ANY one of the above clauses wherein a selective inclusion partition implements a geographic context 427 (e.g. one or more attributes 453) established by one or more event-type categories 760 confirmed by one or more decision-making entities that previously received context-indicative data 294 (at least some of which was) from a context-indicative sensor 234 used with said second wearable article 240 as a component of a data distillation 978, 1178 of a distribution 900, 1100 of second-type articles 240, 840.

37. The method of ANY one of the above clauses wherein a selective inclusion partition implements a kinematic context 427 (e.g. one or more attributes 453) established by one or more event-type categories 760 confirmed by one or more decision-making entities that previously received context-indicative data 294 (at least some of which was) from a context-indicative sensor 234 used with said second wearable article 240 as a component of a data distillation 978, 1178 of a distribution 900, 1100 of second-type articles 240, 840.

38. The method of ANY one of the above clauses wherein a selective inclusion partition implements a time-of-day context 427 (e.g. afternoon or night) established by one or more event-type categories 760 confirmed by one or more decision-making entities that previously received context-indicative data 294 (at least some of which was) from a context-indicative sensor 234 used with said second wearable article 240 as a component of a data distillation 978, 1178 of a distribution 900, 1100 of second-type articles 240, 840.

39. The method of ANY one of the above clauses wherein a selective inclusion partition implements a demographic context 427 (e.g. one or more attributes 453) established by one or more event-type categories 760 confirmed by one or more decision-making entities that previously received context-indicative data 294 (at least some of which was) from a context-indicative sensor 234 used with said second wearable article 240 as a component of a data distillation 978, 1178 of a distribution 900, 1100 of second-type articles 240, 840.

40. The method of ANY one of the above clauses wherein a decision-making entity that received context-indicative data 294 and thereafter provided one or more operating parameters 224, authorizations, or other update components 807 included one or more human evaluators 815.

41. The method of ANY one of the above clauses wherein a decision-making entity that received context-indicative data 294 and thereafter provided one or more operating parameters 224, authorizations, or other update components 807 included one or more machine learning modules 267, intelligence amplification, or other artificial intelligence circuitry 222.

42. The method of ANY one of the above clauses wherein a selective (inclusion partition negatively or otherwise implementing at least one) attribute 427 is established by one or more event-descriptive categories 760 confirmed by a decision-making entity that has received photographic data 294 (at least some of which was) from a camera 718 not aboard the second wearable article 240.

43. The method of ANY one of the above clauses wherein at least one context-indicative sensor 234 used with (at least) the second wearable article 240 is a camera 718 aboard the second wearable article 240 and wherein a selective (inclusion partition negatively or otherwise implementing at least one) attribute 427 is established by one or more event-descriptive categories 760 confirmed by several evaluators 815 who have been shown photographic data 294 (at least some of which was) from a camera 718 not aboard the second wearable article.

44. The method of ANY one of the above clauses wherein a selective (inclusion partition implementing at least one) attribute 427 is established by one or more event-descriptive categories 760 confirmed by (responses 287 establishing a sufficient consensus of) one or more decision-making entities that have been shown photographic data 294 (at least some of which) showed a limb 208A upon which the second wearable article 240 was supported.

45. The method of ANY one of the above clauses wherein at least one context-indicative sensor 234 used with the second wearable article 240 is a camera 718 aboard the second wearable article 240, 840.

46. The method of ANY one of the above clauses wherein a selective inclusion partition implementing a visually apparent attribute 453 is established by one or more event-descriptive categories 760 identified/confirmed by (a sufficient consensus of) several crowdworker evaluators 815 having been shown photographic data 702 from second-type articles 240, 840 that include the second wearable article 240, 840.

47. The method of ANY one of the above clauses wherein a second threshold 752 is a duration-related threshold 752 that affects what magnitude 741 of a rate 765 is deemed "suboptimal" and thereby affects when a first haptic notification 298 based on first sensor data 701 occurs.

48. The method of ANY one of the above clauses wherein the first threshold 752 is a first occurrence count threshold 752 and wherein the suboptimal rate 765 is detected by an occurrence count 754 crossing or otherwise reaching the first occurrence count threshold 752.

49. The method of ANY one of the above clauses wherein one or more machine learning modules have been applied (e.g. as a preparatory operation) to a learning data distillation so as to obtain an updated operating parameter 124, 224 for use in a rule 821 that was previously implemented and by which a behavior event 763 is thereby detected as a suboptimal first-type event that selectively triggers the first haptic notification 298.

50. The method of ANY one of the above clauses comprising:
    invoking transistor-based circuitry configured to initiate a hydration-related haptic notification 298 via the first wearable article 140, 840A automatically and conditionally (at least partly) based on first sensor data 701 aboard the first wearable article 140, 840A signaling that a first (speculative or other) water drinking frequency 751 (e.g. indicative of a hydration-related occurrence count 754 of suboptimal hydration-indicative events 763) detected via the first wearable article 140, 840A has crossed or otherwise reached a hydration-related threshold 752.

51. The method of ANY one of the above clauses comprising:
    invoking transistor-based circuitry (e.g. invocation module 866) configured to initiate a real-time hydration-related haptic notification 298 via the first wearable article 140, 840A.

52. The method of ANY one of the above clauses comprising:
    invoking transistor-based circuitry (e.g. control and invocation modules 864, 866 jointly) configured to initiate a hydration-related haptic notification 298 via the first wearable article 140, 840A automatically and conditionally based on first sensor data 701 aboard the first wearable article 140, 840A (directly or otherwise) signaling that a suboptimal rate 765 of hydration-indicative events 763 has been manifested by a hydration-related threshold 752 (having been crossed or otherwise reached) aboard the first wearable article 140, 840A.

53. The method of ANY one of the above clauses wherein a hydration-related haptic notification 298 delivered via the first wearable article 140, 340A, 840A is haptically distinct from one or more other haptic notifications 298 also delivered via the first wearable article 140, 340A, 840A by virtue of the hydration-related haptic notification 298 including a first distinct pulse sequence symbol 329.

54. The method of ANY one of the above clauses wherein a hydration-related haptic notification 298 is haptically distinct from one or more other haptic notifications 298 (actually) delivered via the first wearable article 140, 340A, 840A by virtue of the hydration-related haptic notification 298 including a first distinct symbol 329 not present in another haptic notification 298 previously delivered via the first wearable article 140, 340A, 840A.

55. The method of ANY one of the above clauses wherein a hydration-related haptic notification 298 is haptically distinct (i.e. distinguishable from any other haptic notifications defined by a protocol) by virtue of including a Morse Code symbol 329.

56. The method of ANY one of the above clauses wherein a hydration-related haptic notification 298 is haptically distinct from one or more other haptic notifications 298 delivered via the first wearable article 140, 340A, 840A by virtue of the hydration-related haptic notification 298 including a first pulse sequence symbol 329 not present in another haptic notification 298 delivered via the first wearable article 140, 340A, 840A.

57. The method of ANY one of the above clauses wherein a hydration-related haptic notification 298 is haptically distinct from one or more other haptic notifications 298 (actually) delivered via the first wearable article 140, 340A, 840A by virtue of the hydration-related haptic notification 298 including a first pulse sequence symbol 329 not present in another haptic notification 298 delivered via the first wearable article 140, 340A, 840A.

58. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set (e.g. a manufacturing lot or other large-enough group 822, 823); wherein a first article set was thereafter used in a particular context 427 that is defined (i.e. separated from indiscriminate sensor data 702) by one or more event attributes 453 to generate a first learning data distillation 778; and wherein one or more (neural network or other) learning modules 267 (e.g. comprising artificial intelligence circuitry 222) have been applied to the first learning data distillation 778 so as to (generate, select, or otherwise) obtain a suitably updated operating parameter 124, 224 for subsequent use in a rule 821A that is actually implemented in the first wearable article 140 or is actually implemented in the second wearable article (or in both) by which a behavior event 763 is thereby detected as a suboptimal first-type event 763.

59. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein a first article set was thereafter used in a particular context 427 that is defined (i.e. separated from indiscriminate sensor data 702) by one or more event attributes 453 to generate a first learning data distillation 778; and wherein one or more (neural network or other machine) learning modules 267 (e.g. comprising artificial intelligence circuitry 222) have been applied to the first learning data distillation 778 so as to (generate, select, or otherwise) obtain a suitably updated operating parameter 124, 224 for subsequent use in a rule 821A that is implemented in the first wearable article 140 or in the second wearable article by which a behavior event 763 is thereby detected as a suboptimal first-type event 763.

60. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more (neural network or other machine) learning modules 267 (e.g. comprising artificial intelligence circuitry 222) have been applied to the first learning data distillation 778 so as to (generate, select, or otherwise) obtain a suitably updated operating parameter 124, 224 (for subsequent use) in a rule 821A that is implemented in the first wearable article 140 or in the second wearable article by which a behavior event 763 is thereby detected as a suboptimal first-type event 763.

61. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set (e.g. a manufacturing lot or other large-enough group 822, 823); wherein the first article set was thereafter used in a particular context 427 that is defined (i.e. separated from indiscriminate sensor data 702) by one or more event attributes 453 to generate a first learning data distillation 778; and wherein one or more (neural network or other machine) learning modules 267 (e.g. comprising artificial intelligence circuitry 222) have been applied to the first learning data distillation 778 so as to (generate, select, or otherwise) obtain a suitably updated magnitude 741 (e.g. as an operating parameter 124, 224 for subsequent use) in a rule 821A that is implemented in the first wearable article 140 or in the second wearable article (or in both) by which a behavior event 763 is thereby detected as a suboptimal first-type event 763.

62. The method of ANY one of the above clauses wherein one or more machine learning modules have been applied (e.g. as a preparatory operation) to characterize how a behavioral event 763 is detectable via a primary or other sensor aboard each of numerous second-type articles 840 of a particular article set; wherein the particular article set was thereafter used in a particular context 427 that is defined (i.e. separated from indiscriminate sensor data 702) by one or more event attributes 453 to generate a first learning data distillation 778; and wherein one or more learning modules 267 (e.g. comprising artificial intelligence circuitry 222) have been applied to the first learning data distillation 778 so as to obtain a suitably updated phase 742 (e.g. as an operating parameter 124, 224 for subsequent use) in a rule 821A that is implemented in the first wearable article 140 or in the second wearable article by which a behavior event 763 is thereby detected as a suboptimal first-type event 763.

63. The method of ANY one of the above clauses wherein one or more machine learning modules have been applied (e.g. as a preparatory operation) to characterize how a behavioral event 763 is detectable via a microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more learning modules 267 (e.g. comprising artificial intelligence circuitry 222) have been applied to the first learning data distillation 778 so as to (generate, select, or otherwise) obtain a suitably updated phase 742 (e.g. as an operating parameter 124, 224 for subsequent use) in a rule 821A that is implemented in the first wearable article 140 or in the second wearable article by which a behavior event 763 is thereby detected as a suboptimal first-type event 763.

64. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more (neural network or other machine) learning modules 267 (e.g. comprising artificial intelligence circuitry 222) have been applied to the first learning data distillation 778 so as to (generate, select, or otherwise) obtain a suitably updated period 743 (e.g. as an operating parameter 124, 224 for subsequent use) in a rule 821A that is implemented in the first wearable article 140 or in the second wearable article by which a behavior event 763 is thereby detected as a suboptimal first-type event 763.

65. The method of ANY one of the above clauses wherein one or more machine learning modules 267 have been applied (e.g. as a preparatory operation) to characterize how a behavioral event 763 affects a first microphone 231 or other sensor 232-234 aboard each of numerous second-type articles 840 of a first article set (e.g. a manufacturing lot or other large-enough group 822, 823); wherein the first article set was thereafter used in a particular context 427 that is defined (i.e. separated from indiscriminate sensor data 702) by one or more event attributes 453 to generate a first learning data distillation 778; and wherein one or more (neural network or other machine) learning modules 267 (e.g. comprising artificial intelligence circuitry 222) have been applied to the first learning data distillation 778 so as to (generate, select, or otherwise) obtain a suitably updated range 745 (e.g. as an operating parameter 124, 224 for subsequent use) in a rule 821A that is implemented in the first wearable article 140 or in the second wearable article (or in both) by which a behavior event 763 is thereby detected as a suboptimal first-type event 763.

66. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more learning modules 267 (e.g. comprising artificial intelligence circuitry 222) have been applied to the first learning data distillation 778 so as to (generate, select, or otherwise) obtain a suitably updated frequency 751 (e.g. as an operating parameter 124, 224 for subsequent use) in a rule 821A that is implemented in the first wearable article 140 or in the second wearable article by which a behavior event 763 is thereby detected as a suboptimal first-type event 763.

67. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more (neural network or other machine) learning modules 267 (e.g. comprising artificial intelligence circuitry 222) have been applied to the first learning data distillation 778 so as to (generate, select, or otherwise) obtain a suitably updated threshold 752 (e.g. as an operating parameter 124, 224 for subsequent use) in a rule 821A that is implemented in the first wearable article 140 or in the second wearable article by which a behavior event 763 is thereby detected as a suboptimal first-type event 763.

68. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set (e.g. a manufacturing lot or other large-enough group 822, 823); wherein the first article set was thereafter used in a particular context 427 that is defined (i.e. separated from indiscriminate sensor data 702) by one or more event attributes 453 to generate a first learning data distillation 778; and wherein one or more (convolutional neural network or other) learning modules 267 (e.g. comprising artificial intelligence circuitry 222) have been applied to the first learning data distillation 778 so as to (generate, select, or otherwise) obtain an improved operating parameter 124, 224 for subsequent use in a rule 821A that is implemented in the first wearable article 140 or in the second wearable article by which a behavior event 763 is thereby detected as a suboptimal first-type event 763 that thereby selectively triggers a true positive haptic notification 298 as the first haptic notification 298.

69. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more learning modules 267 (e.g. comprising artificial intelligence circuitry 222) have been applied to the first learning data distillation 778 so as to (generate, select, or otherwise) obtain an incrementally improved operating parameter 124, 224 for subsequent use in a rule 821A that is implemented in the first wearable article 140 or in the second wearable article (or in both) by which a behavior event 763 is thereby detected as a suboptimal first-type event 763 that thereby selectively triggers a true positive haptic notification 298 as the first haptic notification 298.

70. The method of ANY one of the above clauses wherein one or more machine learning modules have been applied (e.g. as a preparatory operation) to characterize how a behavioral event 763 affects a first microphone 231 or other sensor 232-234 aboard each of numerous second-type articles 840 of a first article set; wherein the first article set was thereafter used in a particular context 427 that is defined (i.e. separated from indiscriminate sensor data 702) by one or more event attributes 453 to generate a first learning data distillation 778; and wherein one or more (neural network or other) learning modules 267 (e.g. comprising artificial intelligence circuitry 222) have been applied to the first learning data distillation 778 so as to (generate, select, or otherwise) obtain an updated (magnitude 741, phase 742, period 743, range 745, frequency 752, threshold 752, or other) operating parameter 124, 224 for subsequent use in a rule 821A that is implemented in the first wearable article 140 or in the second wearable article by which a behavior event 763 is thereby detected as a suboptimal first-type event 763 that thereby selectively refrains from triggering a false positive second haptic notification 298 (that would have occurred with a less selective criterion 753).

71. The method of ANY one of the above clauses wherein numerous second-type articles 840 (e.g. in group 822) were previously configured to implement an eligible (candidate) first rule 821B that was applied (at least) in a first consumption context 427 so as to generate (a distillation 778 of) first success-indicative data 860B therefrom selectively associated (e.g. in one or more records 814 thereof) with an eligible first rule 821B and with a first consumption context 427 and wherein numerous third-type articles 840 (e.g. in group 823) were previously configured to implement an eligible (candidate) second rule 821B that was applied (at least) in a first consumption context 427 so as to generate (a distillation 778 of) second success-indicative data 860C therefrom selectively associated (e.g. in one or more records 814 thereof) with an eligible second rule 821C and with a first consumption context 427 so as to allow a machine learning module 267 (e.g. configured by one or more evaluators 815 or by artificial intelligence) to use a first and second success-indicative data 860B to select automatically which of a first or second eligible rules 821B-C is to be used (at least) in the first wearable article 140, 340A, 840A thereafter.

72. The method of ANY one of the above clauses wherein one or more evaluators 815 (e.g. physicians or other experts) previously defined a candidate first rule 821B for use in numerous second-type articles 840 (e.g. in group 822) and allowed a distillation 778 of success-indicative data 860B therefrom selectively associated with a first consumption context 427 (i.e. "selective" insofar that it is not associated with at least one other digitally defined context) and also defined a (different) candidate second rule 821C for use in numerous third-type articles 840 (e.g. in group 823) and allowed a distillation 778 of success-indicative data 860C therefrom also selectively associated with a first consumption context 427 so as to allow a machine learning module 267 to select or otherwise indicate which of a first or second candidate rules 821B-C was more effective in a first consumption context 427 and is to be used in the first wearable article 140, 340A, 840A for use thereafter (at least) in a first consumption context 427.

73. The method of ANY one of the above clauses wherein a first haptic notification 298 comprises (one or more repetitions of) a first symbol 329 that signals (that a wearer was apparently engaged in) a suboptimal behavior and wherein a subsequent haptic notification 298 comprises another context-specific message with (one or more repetitions of) another symbol 329 that is haptically distinct from that of a first haptic notification 298 (e.g. as distinct as respective Morse Code characters).

74. The method of ANY one of the above clauses wherein a first haptic notification 298 comprises (one or more repetitions of) a first symbol 329 that signals (that a wearer was apparently engaged in) a suboptimal behavior and wherein a subsequent haptic notification 298 signals (that a wearer has apparently completed) a meal or other task without any suboptimal behavior with (one or more repetitions of) another symbol 329 that is haptically distinct from that of a first haptic notification 298 (e.g. as mutually distinct as respective Morse Code characters).

75. The method of ANY one of the above clauses comprising:
  after initiating a first haptic notification 298 (at least partly) based on (one or more kinematic components 703 of) a first sensor data 701 via the first wearable article 140 signaling that an occurrence count 754 of a first-type events 763 (e.g. seconds per bite or other instances of a pattern match 755) detected via the first wearable article 140 has reached an extended (type of) occurrence count threshold 752, automatically invoking transistor-based circuitry configured to end a first haptic notification 298 based on first sensor data 701 aboard the first wearable article 140 signaling that (a rate or other indicia of) first-type events 763 detected via the first wearable article 140 have not continued.

76. The method of ANY one of the above clauses comprising:
  invoking transistor-based circuitry (e.g. an instance of an adaptation module 861) configured to initiate a first haptic notification 298 (at least partly) based on additional sensor data 701 aboard the first wearable article 140 signaling that an occurrence count 754 of first-type events 763 has (apparently crossed or otherwise at least) reached an extended (type of) occurrence count threshold 752 that is larger than or later than a prior first occurrence count 754.

77. The method of ANY one of the above clauses comprising:
  invoking transistor-based circuitry configured to initiate a first haptic notification 298 (at least partly) based on additional sensor data 701 aboard the first wearable article 140 signaling that an occurrence count 754 of first-type events 763 has later reached an extended occurrence count threshold 752 wherein the first wearable article 140 is configured so that an idiothetic kinematic sensor 132 of the first wearable article 140 is identical to an idiothetic kinematic sensor 232 of the second wearable article 240.

78. The method of ANY one of the above clauses comprising:
  invoking transistor-based circuitry configured to initiate a first haptic notification 298 (at least partly) based on additional sensor data 701 aboard the first wearable article 140 signaling that an occurrence count 754 of first-type events 763 has later reached an extended occurrence count threshold 752 wherein the first wearable article 140 is configured so that an idiothetic kinematic sensor 132 of the first wearable article 140 is identical to an idiothetic kinematic sensor 232 of the second wearable article 240.

79. The method of ANY one of the above clauses comprising:
  invoking transistor-based circuitry configured to initiate a first haptic notification 298 (at least partly) based on additional sensor data 701 aboard the first wearable article 140 signaling that an occurrence count 754 of first-type events 763 has later reached an extended occurrence count threshold 752 wherein the first wearable article 140 is configured so that an idiothetic kinematic sensor 132 of the first wearable article 140 is identical to an idiothetic kinematic sensor 232 of the second wearable article 240 but wherein at least one context-indicative sensor 234 used with the second wearable article 240 has no counterpart sensor aboard the first wearable article 140.

80. The method of ANY one of the above clauses comprising:
  invoking transistor-based circuitry configured to initiate a first haptic notification 298 based on additional sensor data 701 aboard the first wearable article 140 signaling that an occurrence count 754 of first-type events 763 has reached an extended occurrence count threshold 752, wherein the first wearable article 140 is configured so that a microphone 131 of the first wearable article 140 is identical to a microphone 231 of the second wearable article 240 but wherein at least one context-indicative sensor 234 used with the second wearable article 240 has no counterpart sensor aboard the first wearable article 140.

81. The method of ANY one of the above clauses wherein detecting that an occurrence count 754 of first-type events 763 aboard the first wearable article 140 has (apparently at least) reached an extended occurrence count threshold 752 comprises:
  observing from a set of one or more second-type articles 840B, 840F sensor data 701 associated with a particular subject 405F (in a context of a behavioral event 763) having one or more qualifying attributes 453A that were present and one or more disqualifying attributes 453 were not present; and
  correlating a first-type article 840A with a sensor data 701 associated with a particular subject 405F having one or more qualifying attributes 453A that are present and one or more disqualifying attributes 453 are not present.

82. The method of ANY one of the above clauses comprising:
  obtaining a first occurrence count threshold 752 by automatically and incrementally adjusting a particular prior occurrence count threshold 752 that was used in initiating a haptic notification 298 via the second wearable article 240 and (at least partly) based on explicit feedback 296 indicating whether or not a particular haptic notification 298 was satisfactory.

83. The method of ANY one of the above clauses comprising:
  obtaining a first occurrence count threshold 752 by automatically and incrementally adjusting a particular occurrence count threshold 752 that was previously used in initiating a haptic notification 298 via the second wearable article 240 and based on explicit Boolean feedback 296 indicating whether or not a particular haptic notification 298 was satisfactory wherein the explicit feedback 296 was associated with context-indicative data 294 relating to a human subject 205 who wore the second wearable article 240.

84. The method of ANY one of the above clauses comprising:
  obtaining a first occurrence count threshold 752 by automatically and incrementally adjusting a particular occurrence count threshold 752 that was used in initiating a haptic notification 298 via the second wearable article 240 and (at least partly) based on explicit feedback 296 indicating whether or not a particular haptic notification 298 was satisfactory wherein the explicit feedback 296 was obtained from human subject 205 as a response 287 to an emailed questionnaire or other textual query 286.

85. The method of ANY one of the above clauses comprising:
  obtaining a first occurrence count threshold 752 by automatically and incrementally adjusting a particular occurrence count threshold 752 that was used in initiating a haptic notification 298 via the second wearable article 240 and based on explicit feedback 296 indicating whether or not a particular haptic notification 298 was satisfactory wherein one or more crowdworker evaluators 815 were shown context-indicative data 294 (e.g. a video clip depicting a human subject 205 eating, annotated with a situational explanation) and then answered a query 286 (e.g. "Was this haptic actuator fired too soon?") requesting feedback 296.

86. The method of ANY one of the above clauses comprising:
  obtaining a first occurrence count threshold 752 by automatically and incrementally adjusting a particular (prior or other) occurrence count threshold 752 that was used in initiating a haptic notification 298 via the second wearable article 240 and (at least partly) based on explicit feedback 296 indicating that a particular haptic notification 298 was satisfactory as an inference from a duration of a human subject 205 having continued to use the second wearable article 240 by more than a threshold period 743 of time (e.g. longer than an hour and less than a month) after a prior second haptic notification 298.

87. The method of ANY one of the above clauses comprising:
  automatically invoking transistor-based circuitry (e.g. an adaptation module 861) configured to end a first haptic notification 298 (conditionally, at least partly) based on (one or more components 703 of) first sensor data 701 via the first wearable article 140 signaling that a first-type events 763 detected via the first wearable article 140 have (apparently) not continued.

88. The method of ANY one of the above clauses comprising:
  after initiating a first haptic notification 298 (at least partly) based on (one or more kinematic components 703 of) a first sensor data 701 via the first wearable article 140 signaling that an occurrence count 754 of a first-type events 763 (e.g. seconds per nutrient transfer or other instances of a pattern match 755) detected via the first wearable article 140 has (apparently crossed or otherwise) reached an extended (type of) occurrence count threshold 752, automatically invoking transistor-based circuitry configured to end a first haptic notification 298 (conditionally, at least partly) based on (one or more components 703 of) first sensor data 701 via the first wearable article 140 signaling that a first-type events 763 detected via the first wearable article 140 have (apparently) not continued.

89. The method of ANY one of the above clauses comprising:
  configuring (one or more first-type articles 840 including) the first wearable article 140 so that a microphone 131 of the first wearable article 140 is (nominally) identical to a microphone 231 of the second wearable article 240.

90. The method of ANY one of the above clauses comprising: configuring the first wearable article 140 so that an idiothetic kinematic sensor 132 of each of one or more first-type articles 840 including the first wearable article 140 is (nominally) identical to an idiothetic kinematic sensor 232 of at least the second wearable article 240.

91. The method of ANY one of the above clauses wherein one or more first-type articles 840 including the first wearable article 140 are configured so that an idiothetic kinematic sensor 132 of each of one or more first-type articles 840 including the first wearable article 140 is (nominally) identical to a counterpart idiothetic kinematic sensor 232 of each of one or more second-type articles 840 including the second wearable article 240 but wherein at least one context-indicative sensor 234 (aboard or otherwise) used with the second wearable article 240 has no counterpart sensor aboard the first wearable article 140.

92. The method of ANY one of the above clauses wherein a haptic notification 298 via the first wearable article 140, 340A, 840A is implemented as a "real time" response 287 to sensor data 701 from a first microphone 131 of the first wearable article 140, 340A, 840A or to sensor data 701 from a first idiothetic kinematic sensor 132 of the first wearable article 140, 340A, 840A (or both) within less than thirty seconds after a last element of a sensor data 701 is aboard the first wearable article 140, 340A, 840A.

93. The method of ANY one of the above clauses wherein a haptic notification 298 via the first wearable article 140, 340A, 840A is implemented as a real time response 287 to auditory sensor data 701 from a first microphone 131 of the first wearable article 140, 340A, 840A within less than thirty seconds after a last element of auditory sensor data 701 is aboard the first wearable article 140, 340A, 840A.

94. The method of ANY one of the above clauses wherein the first wearable article 140, 340A, 840A has a first actuator 138 that is (nominally) identical to a counterpart first haptic actuator 238 of each of the one or more second-type articles 840 and wherein a haptic notification 298 via the first wearable article 140, 340A, 840A is (at least partly) implemented by powering a first actuator 138 of the first wearable article 140, 340A, 840A.

95. The method of ANY one of the above clauses comprising:
determining whether or not a prior rule 821B that was previously established in the second wearable article 240, 840B will be established as a particular rule 321A, 821A in the first wearable article 140, 340A, 840A without any regard to any (video or other) photographic data captured via or depicting the second wearable article 240, 840B.

96. The method of ANY one of the above clauses comprising:
determining whether or not a prior rule 821B that was previously established in the second wearable article 240, 840B will be established as a particular rule 321A, 821A in the first wearable article 140, 340A, 840A without any regard to sensor data 702 from any context-indicative sensor 234 aboard the second wearable article 240, 840B and without any regard to any other context-indicative sensor data 702 (depicting, aboard, or otherwise directly) relating to the second wearable article 240, 840B (irrespective of whether or not any such data exists).

97. The method of ANY one of the above clauses comprising:
transmitting a first quantified index 757 of or other distillation 778 of a percentage or other amount 767 of use of a first (group 822 or other) set of second-type articles 840 to one or more evaluators 815 as an automatic and conditional response 287 (at least partly) based on a first quantified index 757 of an amount 767 of use of a first article set of second-type articles 840 (crossing or otherwise) reaching a threshold 752 (e.g. in hours or counted occurrences of an event).

98. The method of ANY one of the above clauses comprising:
transmitting both a distillation 778 of a percentage or other amount 767 of use of a first (group 822 or other) set of one or more second-type articles 840 and a distillation 778 of a percentage or other amount 767 of use of a second (group 823 or other) set of one or more third-type articles 840 to one or more evaluators 815 and thereafter receiving from (at least one of) one or more evaluators 815 an authorization (e.g. as an update component 807A therewith) to implement a particular rule 321A, 821A therein as a duplicate instance of a prior rule 821B previously established in (each of) one or more second-type articles 840 in lieu of implementing a particular rule 321A, 821A therein as a duplicate instance of an other rule 821C previously established in (each of) numerous third-type articles 840, wherein an amount 767 of use of a second (group 823 or other) set was related to an indication 770 that an other rule 821C established in numerous third-type articles 840 was less (accurate, popular, problematic, effective, or otherwise) successful than a prior rule 821B established in numerous second-type articles 840 as determined by an evaluator(s) 815.

99. The method of ANY one of the above clauses comprising:
configuring a first and second wearable articles 140, 240 so that every sensor 132-133 (included in or otherwise) mechanically supported by the first wearable article 140 has an identical counterpart sensor included in the second wearable article 240.

100. The method of ANY one of the above clauses comprising:
configuring a first and second wearable articles 140, 240 so that every sensor 132-133 (included in or otherwise) mechanically supported by the first wearable article 140 has an identical counterpart sensor included in the second wearable article 240 and so that every (microphone 231 or other) sensor 232-233 mechanically supported by the second wearable article 240 has an identical counterpart sensor included in the first wearable article 140.

101. The method of ANY one of the above clauses configuring a first and second wearable articles 140, 240 so that the second wearable article 240 includes a first camera 718 and so that the first wearable article 140 does not (include or otherwise support) any cameras; and
transmitting a (sampling or other) distillation 778 of context-indicative (video or other) optical data 294 from a first camera 718 to one or more evaluators 815 and thereafter allowing (at least one of) one or more evaluators 815 to provide a success indication 770 pertaining to (one or more operations or aspects of) the second wearable article 240, 840B.

102. The method of ANY one of the above clauses comprising:
configuring a first and second wearable articles 140, 240 so that the second wearable article 240 includes a first camera 718 and so that the first wearable article 140 does not (include or otherwise support) any cameras; and
transmitting a (sampling or other) distillation 778 of context-indicative (video or other) optical data 294 from a first camera 718 to one or more (crowdworkers or other) evaluators 815 and thereafter allowing (at least one of) the one or more evaluators 815 to provide a success indication 770 pertaining to the second wearable article 240, 840B (at least) by adjusting or providing a success-indicative threshold 752.

103. The method of ANY one of the above clauses wherein whether or not a prior rule 821B (e.g. used in the second wearable article 240, 840) will be established as a particular rule 321A, 821A in the first wearable article 140, 340A, 840A is determined without any regard to any photographic or other context-indicative data 294 captured via the second wearable article 240, 840B.

104. The method of ANY one of the above clauses wherein whether or not a prior rule 821B used in the second wearable article 240, 840B will be established as a particular rule 321A, 821A in the first wearable article 140, 340A, 840A is determined without any regard to any photographic or other context-indicative data 294 depicting the second wearable article 240, 840B.

105. The method of ANY one of the above clauses wherein a quantified index 757 of an amount 767 of use of at least the second wearable article 240, 840B quantifies how much a prior rule 821B was used in (two or more) second-type articles including the second wearable article 240, 840B but disregards at least how much an (earlier) original rule 821 was used in second-type articles including the second wearable article 240, 840B.

106. The method of ANY one of the above clauses wherein a conditional response 287 to an indication 770 of a suboptimal rate 765 of ingestion is "conditional" in the first wearable article 140, 340A, 840A insofar that the conditional response 287 to the indication 770 of the suboptimal rate 765 of ingestion actually results from a suboptimal rate 765 of ingestion (having an indication that resides digitally) in the first wearable article 140, 340A, 840A.

107. The method of ANY one of the above clauses wherein a conditional response 287 to an indication 770 of a suboptimal rate 765 of ingestion is in real time in at least the first wearable article 140, 340A, 840A.

108. The method of ANY one of the above clauses wherein a conditional response 287 to an indication 770 of a suboptimal rate 765 of ingestion is "automatic" in the first wearable article 140, 340A, 840A insofar that the conditional response 287 is derived from sensor data 701 provided by one or more sensors aboard the first wearable article 140, 340A, 840A without regard to any user input 608 that occurs (temporally) between the sensor data 701 and the conditional response 287.

109. The method of ANY one of the above clauses wherein a conditional response 287 to an indication 770 of a suboptimal rate 765 of ingestion is "local" in the first wearable article 140, 340A, 840A insofar that the conditional response 287 is derived aboard the first wearable article 140, 340A, 840A from sensor data 701 provided by one or more sensors aboard the first wearable article 140, 340A, 840A with no signal path therebetween flowing through any resource that is remote (i.e. more than 1 kilometer from) from the first wearable article 140, 340A, 840A.

110. The method of ANY one of the above clauses wherein a first rate 765 is indicated partly based on a first microphone 231 of the second wearable article 240, 840B and partly based (at least) on a first idiothetic kinematic sensor 232 of the second wearable article 240, 840B.

111. The method of ANY one of the above clauses wherein a first rate 765 is indicated partly based on a first microphone 231 of the second wearable article 240, 840B and partly based on a first idiothetic kinematic sensor 232 of the second wearable article 240, 840B and wherein configuring the first wearable article 140, 340A, 840A comprises determining whether or not a prior rule 821B will be established as a particular rule 321A, 821A in the first wearable article 140, 340A, 840A without any regard to any photographic (or other context-indicative) data 294 captured via or depicting the second wearable article 240, 840B.

112. The method of ANY one of the above clauses wherein the allowing the first wearable article 140, 340A, 840A to invoke a particular rule 321A, 821A so as to trigger a haptic notification 298 via the first wearable article 140, 340A, 840A comprises:
    allowing the first wearable article 140, 340A, 840A to invoke a first response protocol 120 that includes first and second rules 820 so as to trigger a haptic notification 298 via the first wearable article 140, 340A, 840A as a conditional response 287 to an indication 770 a suboptimal rate 765 of ingestion, wherein a first rule is a particular rule 321A, 821A.

113. The method of ANY one of the above clauses allowing the first wearable article 140, 340A, 840A to invoke a particular rule 321A, 821A so as to trigger a haptic notification 298 via the first wearable article 140, 340A, 840A comprises:
    allowing the first wearable article 140, 340A, 840A to invoke a particular rule 321A, 821A so as to trigger a haptic notification 298 via the first wearable article 140, 340A, 840A as a local automatic and conditional response 287 to an indication 770 of an (actual or apparent) suboptimal rate 765 of ingestion partly based on (data from) a microphone 131 of the first wearable article 140, 340A, 840A and partly based on (data from) an idiothetic kinematic sensor 132 of the first wearable article 140, 340A, 840A.

114. The method of ANY one of the above clauses wherein the first wearable article 140, 340A, 840A would otherwise be configured (e.g. by a hub 890 that manages a central or regional inventory 808) to establish a particular rule 321A, 821A therein as a duplicate instance of a different rule 821C previously established in numerous third-type articles 840 of an other group 823 (instead of a prior rule 821B) instead as a conditional response 287 (at least partly) based on a first (other index 757, average, or other) distillation 778 of an (other) amount 767 of use of (the different rule 821C in) a third-type articles 840 of an other group 823 having been sent to one or more evaluators 815 and thereafter receiving from the one or more evaluators 815 (at least an indication 770 of) a threshold 752 against which one or more later-obtained use-amount-indicative quantified indexes 757 (e.g. pertaining to a subsequent performance of one or more other (groups or other) sets of substantially similar wearable articles 840B, 840F) are later compared.

115. A haptic feedback support system 100, 200, 300, 400, 500 as described herein and configured to perform one or more of the above-described methods.

116. A haptic feedback support system 100, 200, 300, 400, 500 relating to one or more first-type articles 840 including a (particular) first wearable article 140, 840A and also relating to one or more second-type articles 840 that include a first (factory lot or other) set of one or more second-type articles 840 of the one or more second-type articles 840, wherein a first article set includes at least a (particular) second wearable article 240, 840B and wherein a method comprises:
    transistor-based circuitry (e.g. a deployment module 268 implemented in a hub 890 that manages a central or regional inventory 809 of articles) configured to cause the first wearable article 140, 340A, 840A (e.g. via hub 890 as shown in FIG. 8) to receive a particular rule 321A, 821A therein as a duplicate instance of a prior rule 821B previously established in (each of) numerous second-type articles 840 as a conditional response 287 (at least partly) based on a first quantified index 757 of an amount 767 of use of a first article set of the one or more second-type articles 840 (singly or collectively crossing or otherwise) reaching a threshold 752.

117. The system of ANY one of the above clauses comprising:
    the first wearable article 140, 340A, 840A.

118. The system of ANY one of the above clauses comprising:
    the one or more first-type articles 840 including the first wearable article 140, 340A, 840A; and
    a hub operably coupled to a local inventory 809 that includes the one or more first-type articles 840 and configured to distribute one or more update components 807A to each wearable article 840 of a local inventory 809.

119. The system of ANY one of the above clauses wherein a first idiothetic kinematic sensor 132 of the first wearable article 140, 340A, 840A is an accelerometer 716 or a tiltometer 717.

With respect to the numbered claims expressed below, those skilled in the art will appreciate that recited operations therein may generally be performed in any order. Also, although various operational flows are presented in sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other such transitive, relational, or other connections do not generally exclude such variants, unless context dictates otherwise.

What is claimed is:

1. A haptic feedback support method relating to one or more first-type articles including a first wearable article configured to be worn on a limb of a first human subject and also relating to numerous second-type articles that include a first set of said second-type articles, wherein said first set includes at least a second wearable article and wherein said method comprises:

invoking transistor-based artificial intelligence circuitry configured to cause said first wearable article to receive a particular rule therein as another instance of a prior rule previously established in said numerous second-type articles as a conditional response based on a first quantified index of an amount of use of said first set of said second-type articles reaching a corresponding success-indicative threshold including allowing said prior rule to trigger a haptic notification via second wearable article as a local automatic and conditional response to an indication of a suboptimal rate of ingestion partly based on a first microphone of said second wearable article and partly based on a first idiothetic kinematic sensor of said second wearable article, wherein said configuring said first wearable article comprises determining whether or not said prior rule will be established as said particular rule in said first wearable article without any regard to any photographic data captured via or depicting said second wearable article; and invoking transistor-based artificial intelligence circuitry configured to allow said first wearable article to invoke said particular rule so as to trigger a haptic notification via said first wearable article as a local automatic and conditional response to an indication of a suboptimal rate of ingestion in said first wearable article partly based on a first microphone of said first wearable article and partly based on a first idiothetic kinematic sensor of said first wearable article, wherein said first wearable article has a first actuator that is identical to a counterpart first haptic actuator of each of said numerous second-type articles and wherein said haptic notification via said first wearable article is implemented by powering said first actuator of said first wearable article as a real time response to sensor data aboard said first wearable article within less than thirty seconds after a last element of said sensor data is aboard said first wearable article.

2. The method of claim 1 wherein said determining whether or not said prior rule that was previously established in said second wearable article will be established as said particular rule in said first wearable article comprises:

determining whether or not said prior rule that was previously established in said second wearable article will be established as said particular rule in said first wearable article without any regard to any sensor data from any context-indicative sensor aboard said second wearable article and without any regard to any other context-indicative sensor data depicting, obtained via, or otherwise relating to said second wearable article.

3. The method of claim 1 wherein said first wearable article would otherwise be configured to establish said particular rule therein as another instance of a different rule previously established in numerous third-type articles of another set instead as a conditional response based on a first distillation of an amount of use of said third-type articles of said other set having been sent to one or more evaluators and thereafter receiving from said one or more evaluators said success-indicative threshold against which one or more use-amountindicative quantified indexes are later compared.

4. The method of claim 1 comprising:

configuring said first and second wearable articles so that every sensor mechanically supported by said first wearable article is identical to a counterpart sensor included in said second wearable article and so that said first and second wearable article both do not include or otherwise support any cameras.

5. The method of claim 1 comprising:

configuring said first and second wearable articles so that said second wearable article includes a first camera and so that said first wearable article does not include any cameras; and transmitting a distillation of context-indicative optical data from said first camera to one or more crowdworker evaluators and thereafter allowing said one or more crowdworker evaluators to provide a success indication pertaining to said second wearable article by adjusting or providing said success-indicative threshold.

6. The method of claim 1 wherein said first wearable article has a first microphone that is identical to a counterpart first microphone of each of said numerous second-type articles in said first set, wherein said haptic notification via said first wearable article is caused by said first microphone influencing said indication of said suboptimal rate of ingestion, wherein said first wearable article has a first idiothetic kinematic sensor that is identical to a counterpart first idiothetic kinematic sensor of each of said numerous secondtype articles in said first set, and wherein said haptic notification via said first wearable article is caused by said first idiothetic kinematic sensor influencing said indication of said suboptimal rate of ingestion.

7. A haptic feedback support method relating to one or more first-type articles including a first wearable article configured to be worn on a limb of a first human subject and also relating to numerous second-type articles that include a set of said second-type articles, wherein a second wearable article is one of said set of said second-type articles and wherein said method comprises:

invoking transistor-based circuitry configured to cause said first wearable article to receive a particular rule therein as another instance of a prior rule previously established in said numerous second-type articles as a conditional response based on a first quantified index of an amount of use of said set of said one or more second-type articles reaching a threshold including allowing said prior rule to trigger a haptic notification via second wearable article as a conditional response to an indication of a rate of ingestion; and invoking transistor-based circuitry configured to allow said first wearable article to invoke said particular rule so as to trigger a haptic notification via said first wearable article as a local automatic and conditional response to an indication of a suboptimal rate of ingestion in said first wearable article, wherein said first wearable article has a first actuator that is identical to a counterpart first haptic actuator of each of said numerous second-type articles and wherein said haptic notification via said first wearable article is implemented by powering said first actuator of said first wearable article.

8. The method of claim 7 wherein said haptic notification via said first wearable article is implemented by powering said first actuator of said first wearable article as a real time response to sensor data aboard said first wearable article within less than thirty seconds after a last element of said sensor data is aboard said first wearable article.

9. The method of claim 7 wherein second wearable article is configured to include a first microphone and wherein said indication of said rate of ingestion is determined partly based on said first microphone of said second wearable article.

10. The method of claim 7 wherein said indication of said rate of ingestion is determined partly based on a first microphone of said second wearable article and partly based on a first idiothetic kinematic sensor of said second wearable article and wherein configuring said first wearable article comprises determining whether or not said prior rule will be established as said particular rule in said first wearable article without any regard to any photographic data captured via or depicting said second wearable article.

11. The method of claim 7 wherein said conditional response to said indication of said suboptimal rate of ingestion is automatic and local in said first wearable article and wherein configuring said first wearable article comprises determining whether or not said prior rule will be established as said particular rule in said first wearable article without any regard to any photographic data captured via or depicting said second wearable article.

12. The method of claim 7 wherein said allowing said first wearable article to invoke said particular rule so as to trigger a haptic notification via said first wearable article comprises:
allowing said first wearable article to invoke a first response protocol that includes first and second rules so as to trigger said haptic notification via said first wearable article as said conditional response to said indication said suboptimal rate of ingestion, wherein said first rule is said particular rule.

13. The method of claim 7 wherein said allowing said first wearable article to invoke said particular rule so as to trigger a haptic notification via said first wearable article comprises:
allowing said first wearable article to invoke said particular rule so as to trigger a haptic notification via said first wearable article as a conditional response to an indication of an suboptimal rate of ingestion partly based on a microphone of said first wearable article and partly based on a particular first sensor of said first wearable article.

14. The method of claim 7 comprising:
invoking transistor-based circuitry configured to initiate a hydration-related haptic notification via said first wearable article automatically and conditionally based on first sensor data aboard said first wearable article signaling that a hydration-related scalar indication detected via said first wearable article has reached a hydration-related threshold, wherein said hydration-related haptic notification is haptically distinguishable from said haptic notification via said first wearable article as said local automatic and conditional response to said indication of said suboptimal rate of ingestion in said first wearable article.

15. A haptic feedback support system relating to one or more first-type articles including a first wearable article configured to be worn on a limb of a first human subject and also relating to numerous second-type articles that include a set of said second-type articles, wherein a second wearable article is one of said set of said second-type articles and wherein said system comprises:
transistor-based circuitry configured to cause said first wearable article to receive a particular rule therein as another instance of a prior rule previously established in said numerous second-type articles as a conditional response based on a first quantified index of an amount of use of said set of said second-type articles reaching a threshold including allowing said prior rule to trigger a haptic notification via second wearable article as a conditional response to an indication of a rate of ingestion; and
transistor-based circuitry configured to allow said first wearable article to invoke said particular rule so as to trigger a haptic notification via said first wearable article as a local automatic and conditional response to an indication of a suboptimal rate of ingestion in said first wearable article, wherein said first wearable article has a first actuator that is identical to a counterpart first haptic actuator of each of said numerous second-type articles and wherein said haptic notification via said first wearable article is implemented by powering said first actuator of said first wearable article.

16. The system of claim 15 comprising:
said first and second wearable articles, wherein a first idiothetic kinematic sensor of said first wearable article is an accelerometer or a tiltometer and wherein a first idiothetic kinematic sensor of said second wearable article is also an accelerometer or a tiltometer, matched to said first idiothetic kinematic sensor of said first wearable article.

17. The system of claim 15 comprising:
said first and second wearable articles configured so that every sensor mechanically supported by said first wearable article has an identical counterpart sensor included in said second wearable article and so that every sensor mechanically supported by said second wearable article has an identical counterpart sensor included in said first wearable article.

* * * * *